(12) United States Patent
Onuma

(10) Patent No.: US 9,566,080 B2
(45) Date of Patent: Feb. 14, 2017

(54) GRASPING TREATMENT DEVICE

(71) Applicant: OLYMPUS CORPORATION, Hachioji-shi, Tokyo (JP)

(72) Inventor: Ryu Onuma, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 896 days.

(21) Appl. No.: 13/857,542

(22) Filed: Apr. 5, 2013

(65) Prior Publication Data

US 2013/0304105 A1 Nov. 14, 2013

Related U.S. Application Data

(60) Provisional application No. 61/623,270, filed on Apr. 12, 2012.

(51) Int. Cl.
| | | |
|---|---|---|
| A61B 17/29 | (2006.01) | |
| A61B 17/32 | (2006.01) | |
| A61B 18/14 | (2006.01) | |
| A61B 17/00 | (2006.01) | |
| A61B 17/22 | (2006.01) | |

(52) U.S. Cl.
CPC ....... *A61B 17/29* (2013.01); *A61B 17/320068* (2013.01); *A61B 17/320092* (2013.01); *A61B 18/1445* (2013.01); *A61B 2017/003* (2013.01); *A61B 2017/00424* (2013.01); *A61B 2017/22021* (2013.01); *A61B 2017/2929* (2013.01)

(58) Field of Classification Search
CPC ............ A61B 17/29; A61B 17/320092; A61B 17/320068; A61B 18/1445; A61B 2017/2901–17/2903; A61B 2017/2927; A61B 2017/2929
See application file for complete search history.

(56) References Cited

U.S. PATENT DOCUMENTS

| | | | | |
|---|---|---|---|---|
| 2006/0259054 | A1* | 11/2006 | Masuda | ................. A61B 17/29 606/169 |
| 2009/0171159 | A1* | 7/2009 | Jorgensen | ............ A61B 1/0055 600/139 |
| 2011/0106078 | A1 | 5/2011 | Mueller | |

\* cited by examiner

*Primary Examiner* — Ryan J Severson
*Assistant Examiner* — Anh Dang
(74) *Attorney, Agent, or Firm* — Oliff PLC

(57) ABSTRACT

A grasping treatment device includes a first sheath section, a second sheath section including a bending cylindrical section, and a rotating transmitting portion configured to rotate to allow a grasping section and the first sheath section to rotate in one of periaxial directions of a longitudinal axis with respect to the second sheath section. The grasping treatment device includes an opening/closing transmitting portion configured to move a movable portion of the first sheath section toward a proximal direction with respect to a probe fixed portion by being pulled toward the proximal direction, and an acting force transmitting portion configured to transmit an acting force from the probe fixed portion to the bending cylindrical section, the acting force being configured to act on the probe fixed portion from the movable portion toward the proximal direction.

11 Claims, 17 Drawing Sheets

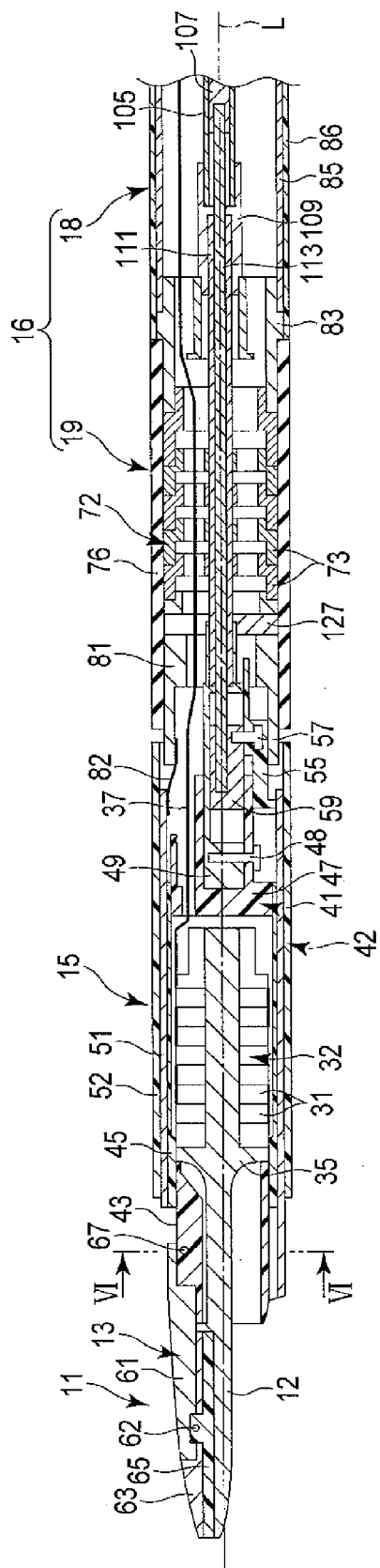
F I G. 2

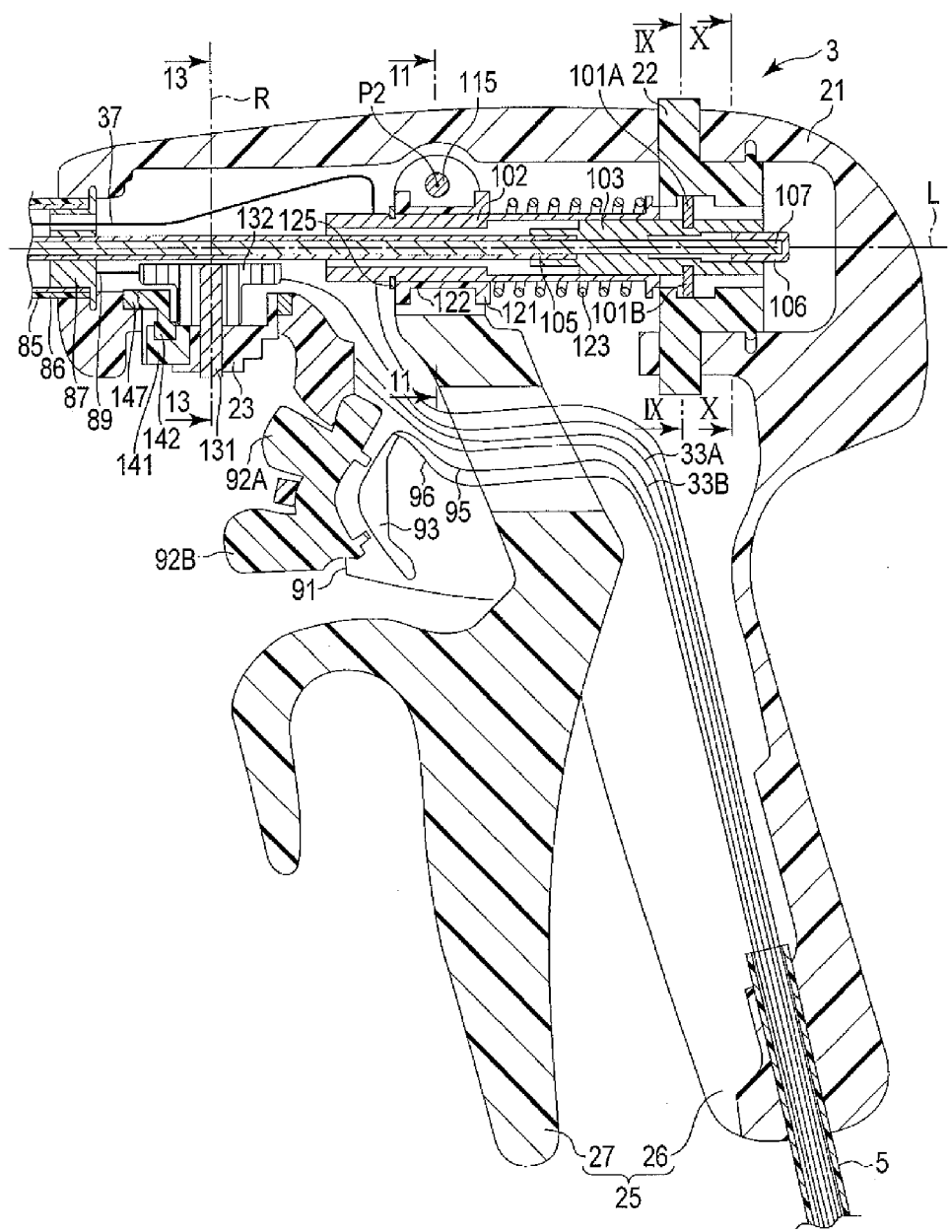
F I G. 4

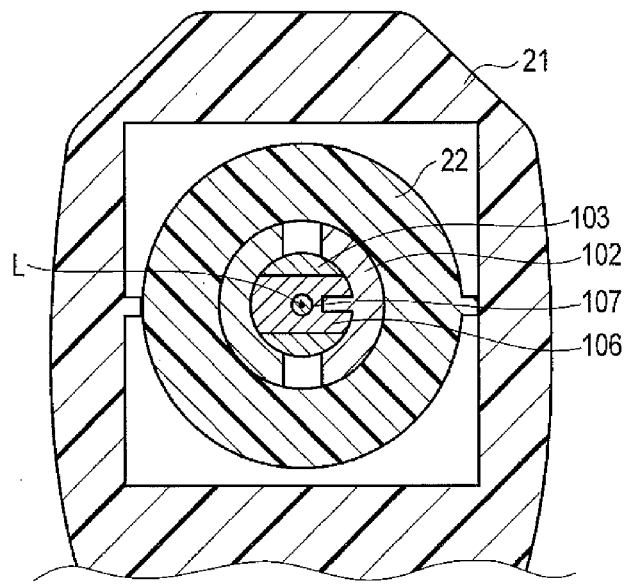
F I G. 10
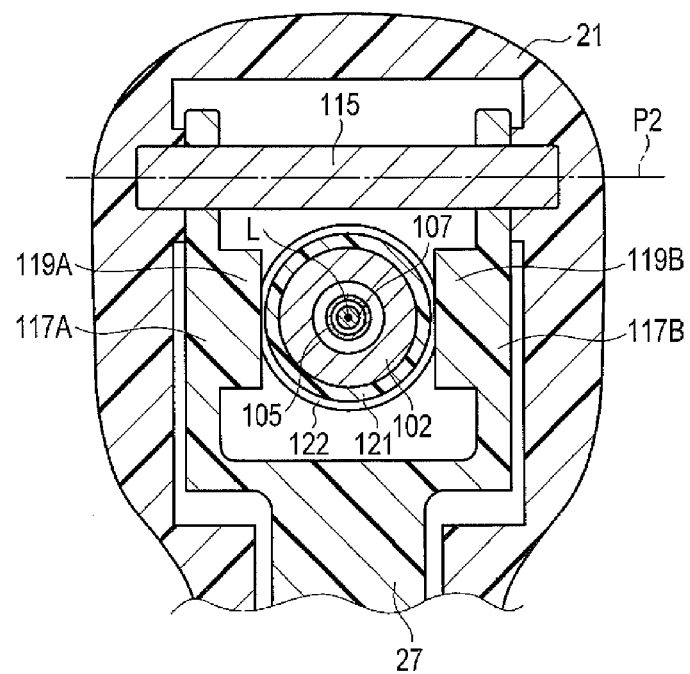
F I G. 11

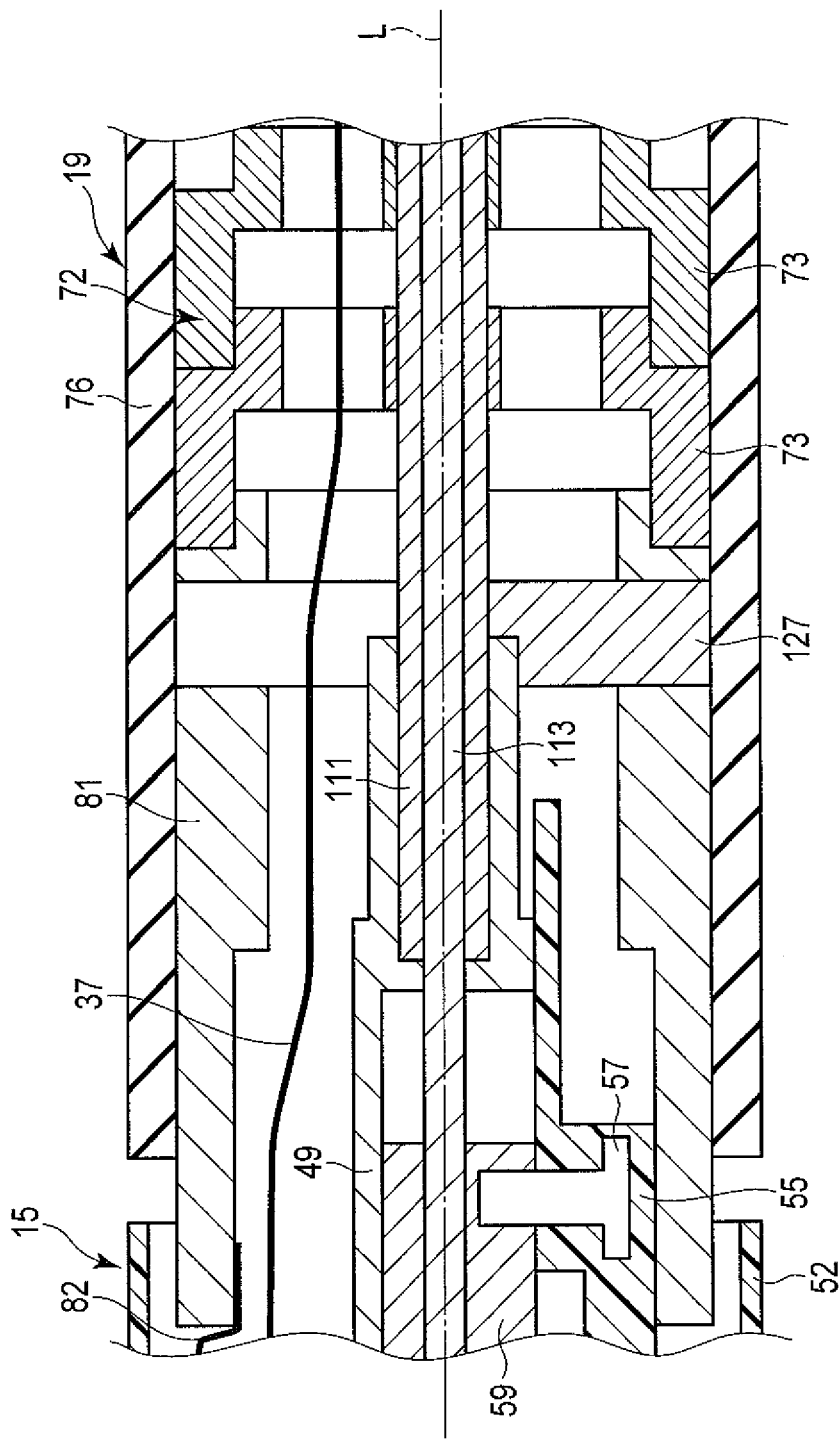
F I G. 12

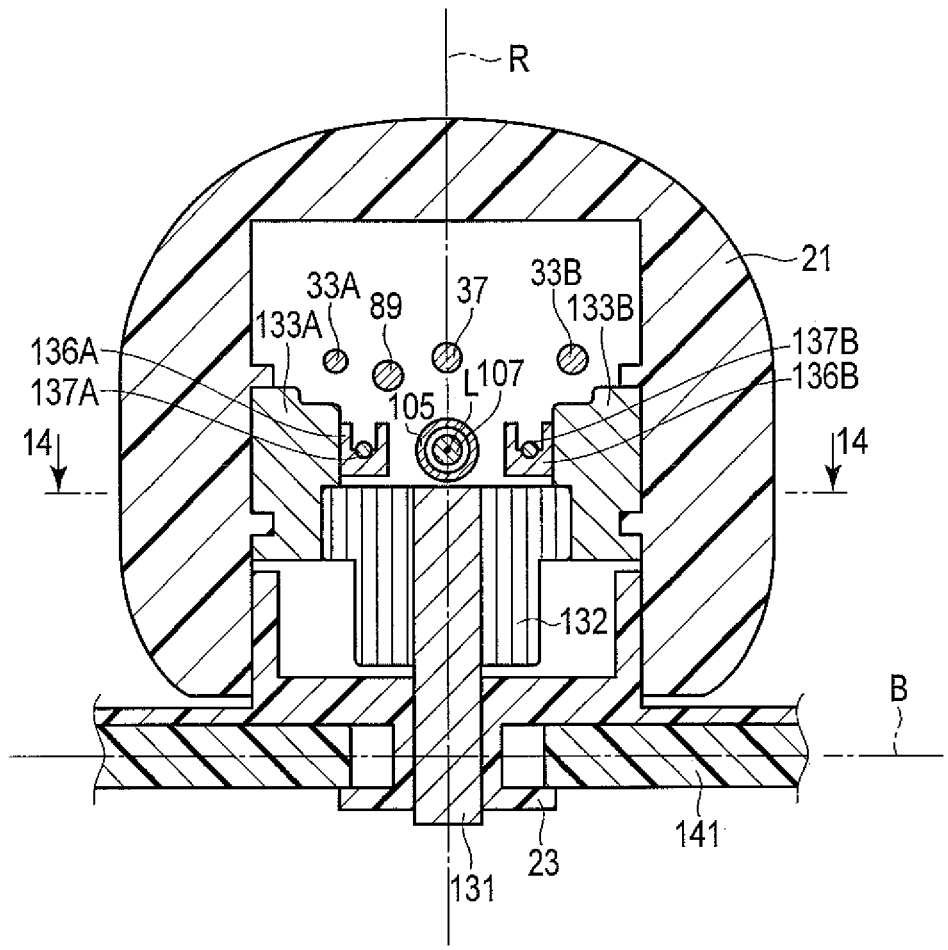
F I G. 13

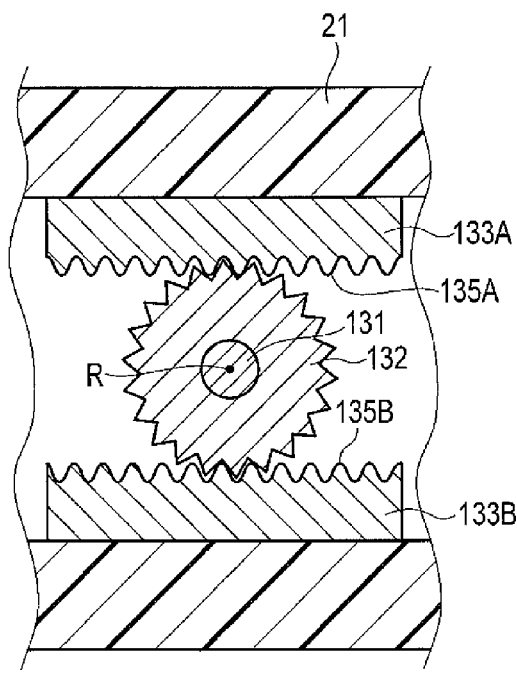
F I G. 14
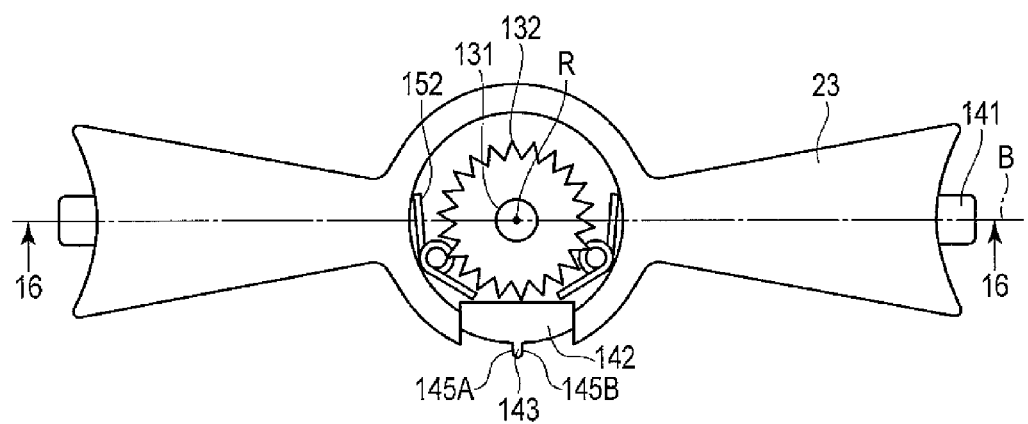
F I G. 15

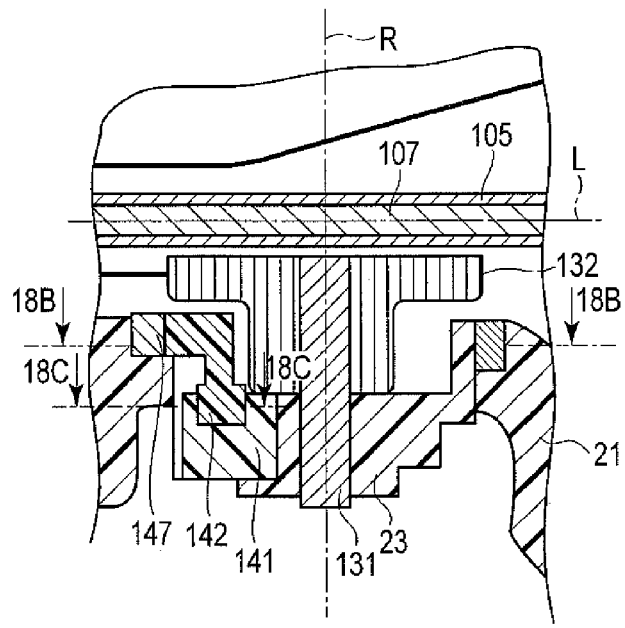
F I G. 18A
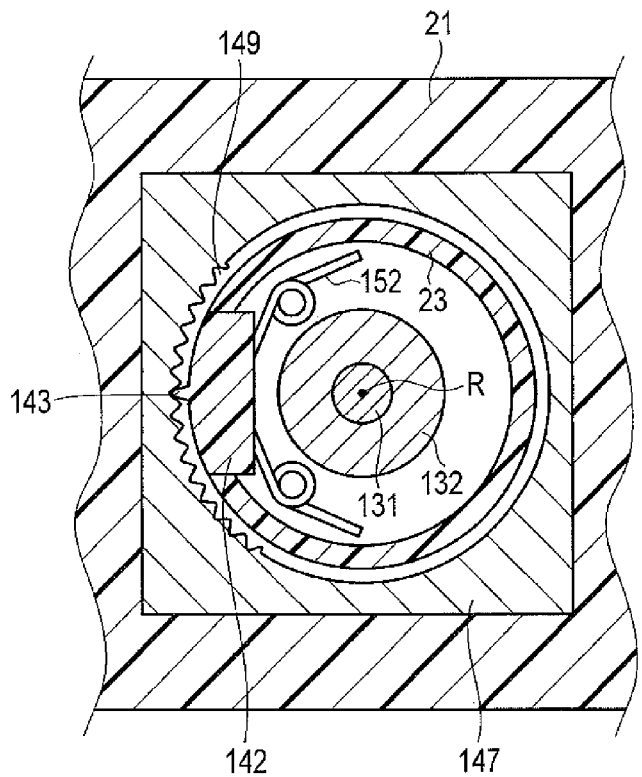
F I G. 18B

GRASPING TREATMENT DEVICE

CROSS-REFERENCE TO RELATED APPLICATIONS

This application is based upon and claims the benefit of priority from prior U.S. Provisional Application No. 61/623,270, filed Apr. 12, 2012, the entire contents of which are incorporated herein by reference.

BACKGROUND OF THE INVENTION

1. Field of the Invention

The present invention relates to a grasping treatment device configured to grasp a grasping target such as a body tissue (biological tissue) by using a grasping section including a probe and a jaw configured to be opened or closed with respect to the probe.

2. Description of the Related Art

US2011/0106078 discloses a grasping treatment device (grasping surgical device) configured to grasp a grasping target such as a body tissue by using a grasping section including a probe and a jaw configured to be opened or closed with respect to the probe. This grasping treatment device includes a first sheath section provided to a proximal direction side of the grasping section, and a second sheath section provided to the proximal direction side of the first sheath section. The grasping section and the first sheath section are rotatable in directions around a longitudinal axis (periaxial directions of the longitudinal axis) with respect to the second sheath section. The second sheath section includes a non-bending cylindrical section, and a bending cylindrical section provided to a distal direction side of the non-bending cylindrical section. When the bending cylindrical section bends, a bending angle of the first sheath section relative to the non-bending cylindrical section varies. An opening/closing wire as an opening/closing transmitting portion is extended in (inside) the second sheath section along the longitudinal axis. When the opening/closing wire moves along the longitudinal axis, the jaw is opened or closed with respect to the probe. As described above, there is configured the grasping treatment device in which the grasping section and the first sheath section, which are provided to the distal direction side of the second sheath section, are rotatable in the periaxial directions of the longitudinal direction with respect to the second sheath section including the bendable bending cylindrical section.

BRIEF SUMMARY OF THE INVENTION

According to one aspect of the invention, a grasping treatment device includes that a grasping section which includes a probe extended along a longitudinal axis, and a jaw which is openable/closeable with respect to the probe; a first sheath section which is extended to a proximal direction side of the grasping section along the longitudinal axis, the first sheath section including a probe fixed portion provided being fixed to the probe, and a movable portion which is connected to the jaw and which is movable with respect to the probe fixed portion along the longitudinal axis; a second sheath section which is provided to the proximal direction side of the first sheath section, the second sheath section including a non-bending cylindrical section which is extended along the longitudinal axis, and a bending cylindrical section which is provided to a distal direction side of the non-bending cylindrical section and which is configured to bend to change a bending angle of the first sheath section relative to the non-bending cylindrical section; a rotating transmitting portion which is extended in the second sheath section along the longitudinal axis, and which is configured to rotate to allow the grasping section and the first sheath section to rotate in one of periaxial directions of the longitudinal axis with respect to the second sheath section; an opening/closing transmitting portion which is extended in the second sheath section along the longitudinal axis, and which is configured to move along the longitudinal axis to enable the jaw to be opened and closed with respect to the probe, the opening/closing transmitting portion being configured to move the movable portion toward the proximal direction with respect to the probe fixed portion by being pulled toward the proximal direction; a guide member which is provided in the bending cylindrical section with the opening/closing transmitting portion being inserted therein, and which is configured to guide the opening/closing transmitting portion; and an acting force transmitting portion which is configured to transmit an acting force from the probe fixed portion to the bending cylindrical section, the acting force being configured to act on the probe fixed portion from the movable portion toward the proximal direction in a state that the movable portion moves toward the proximal direction and the jaw closes relative to the probe.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a cross-sectional view schematically showing an insertion unit according to the first embodiment in a cross-section which runs through a longitudinal axis and which is parallel to a rotating axis of a bending operation lever;

FIG. 4 is a cross-sectional view schematically showing an operation unit according to the first embodiment in a cross-section which runs through the longitudinal axis and which is parallel to the rotating axis of the bending operation lever;

FIG. 10 is a cross-sectional view taken along a line X-X in FIG. 4;

FIG. 11 is a cross-sectional view taken along a line 11-11 in FIG. 4;

FIG. 12 is a cross-sectional view schematically showing a configuration of a coupling portion between the first sheath section and a second sheath section according to the first embodiment in a cross-section which runs though the longitudinal axis and which is parallel to the rotating axis of the bending operation lever;

FIG. 13 is a cross-sectional view taken along a line 13-13 in FIG. 4;

FIG. 14 is a cross-sectional view taken along a line 14-14 in FIG. 13;

FIG. 15 is a plan view schematically showing a configuration of the bending operation lever, a pinion gear, and a bending lock operation bar according to the first embodiment;

FIG. 18A is a cross-sectional view schematically showing a configuration near the bending operation lever of a cylindrical case in a cross-section which runs through the longitudinal axis and which is parallel to the rotating axis of the bending operation lever;

FIG. 18B is a cross-sectional view taken along a line 18B-18B in FIG. 18A;

DETAILED DESCRIPTION OF THE INVENTION

First Embodiment

Figure 1A:
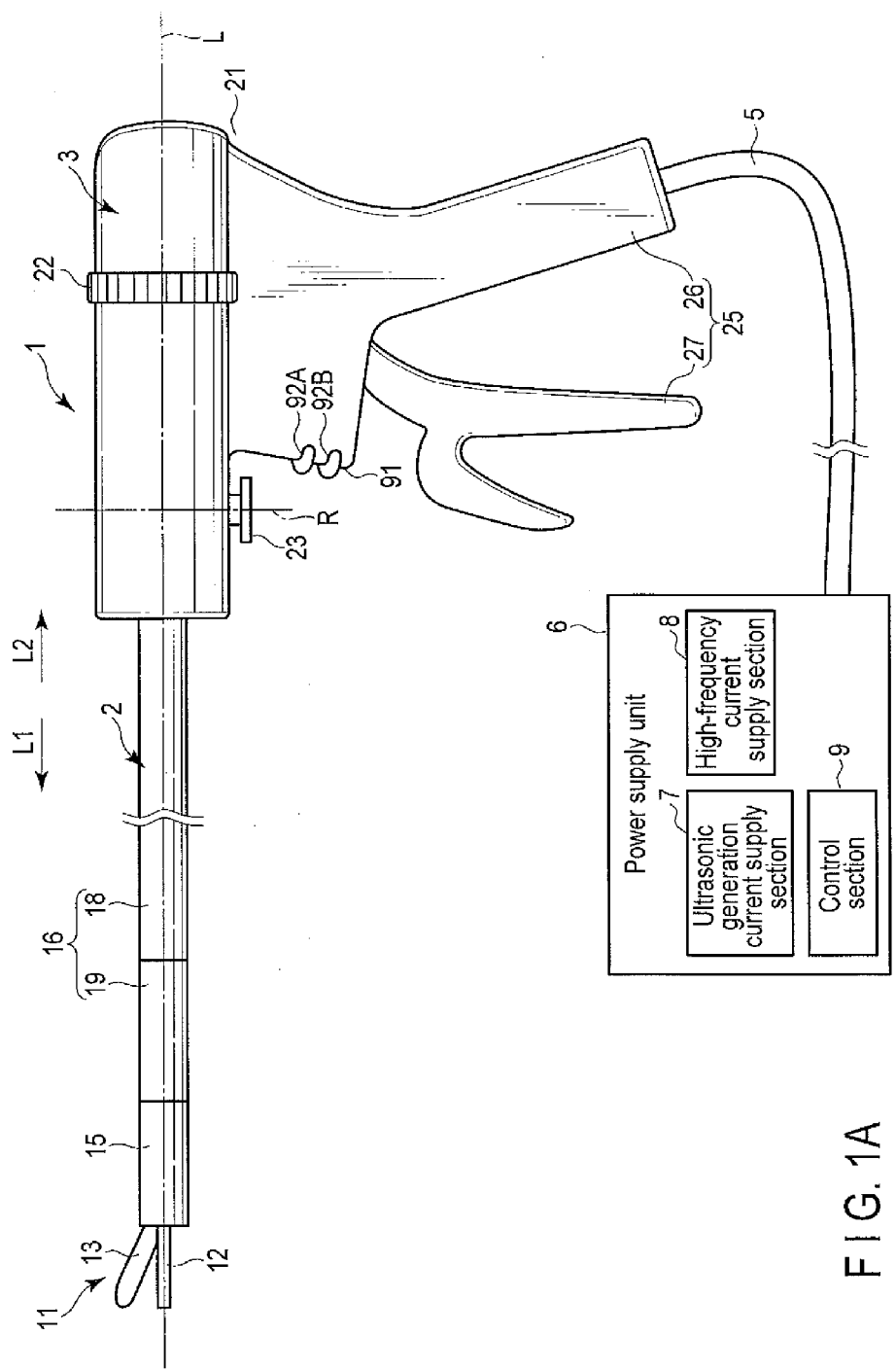
FIG. 1A is a side elevation schematically showing a grasping treatment device according to a first embodiment of the present invention.
Figure 1B:
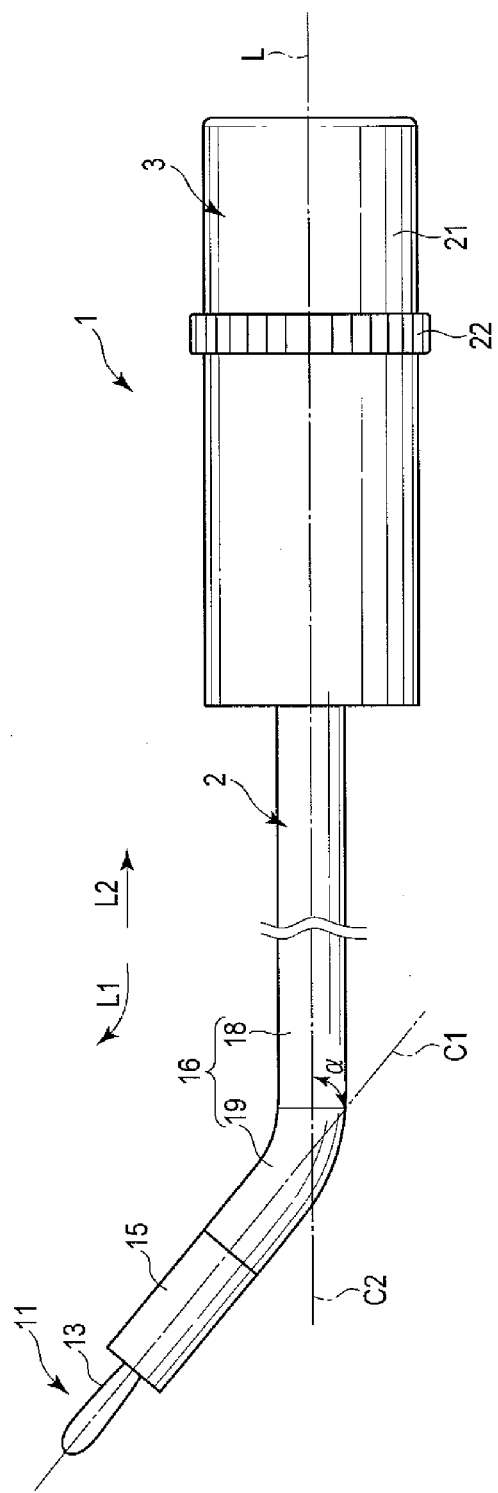
FIG. 1B is a plan view schematically showing the grasping treatment device according to the first embodiment.

A first embodiment according to the present invention will now be described with reference to FIG. 1A to FIG. 21. FIG. 1A and FIG. 1B are views showing a grasping treatment device (grasping surgical device) 1 according to this embodiment. As shown in FIG. 1A and FIG. 1B, the grasping treatment device 1 has a longitudinal axis L. Here, one of two directions parallel to the longitudinal axis L is determined as a distal direction (a direction of an arrow L1 in FIG. 1A and FIG. 1B), and an opposite direction of the distal direction is determined as a proximal direction (a direction of an arrow L2 in FIG. 1A and FIG. 1B).

The grasping treatment device 1 includes an insertion unit 2 extended along the longitudinal axis L, and an operation unit 3 which is provided to the proximal direction side of the insertion unit 2. One end of a cable 5 is connected to the operation unit 3. The other end of the cable 5 is connected to a power supply unit 6. The power supply unit 6 includes an ultrasonic generation current supply section 7, a high-frequency current supply section 8, and a control section 9.

Figure 3:
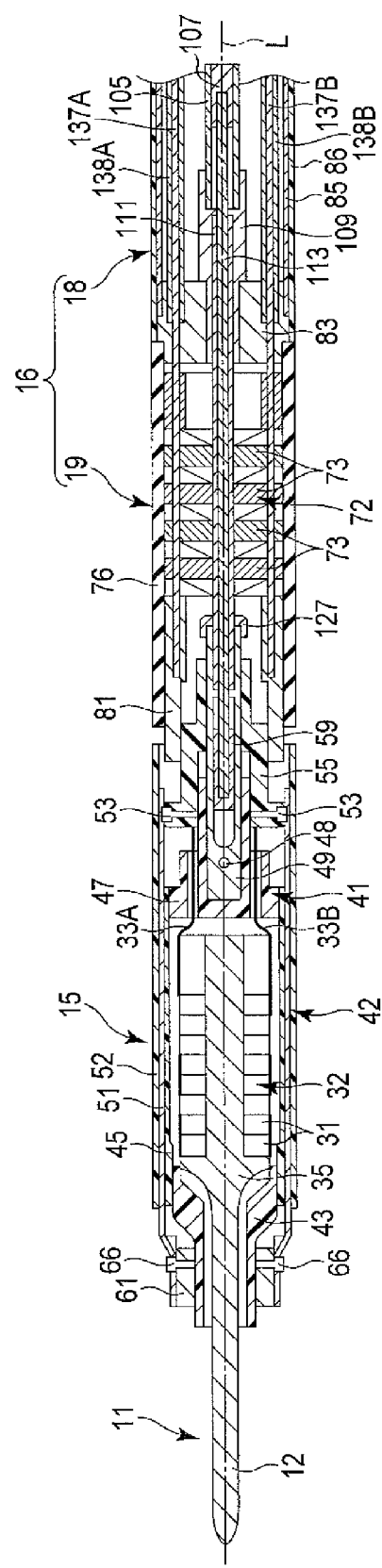
FIG. 3 is a cross-sectional view schematically showing the insertion unit according to the first embodiment in a cross-section which runs through the longitudinal axis and which is perpendicular to the rotating axis of the bending operation lever.

FIG. 2 and FIG. 3 are views showing a configuration of the insertion unit 2. As shown in FIG. 1A to FIG. 3, the insertion unit 2 includes a grasping section 11 configured to grasp a grasping target such as a body tissue (biological tissue). The grasping section 11 includes a probe 12 which is extended along the longitudinal axis L, and a jaw 13 which is configured to be opened or closed with respect to the probe 12. A first sheath section 15 is extended to the proximal direction side of the grasping section 11 along the longitudinal axis L. The probe 12 is inserted into the first sheath section 15 from the distal direction side.

The insertion unit 2 includes a second sheath section 16 provided to the proximal direction side of the first sheath section 15. The grasping section 11 and the first sheath section 15 are rotatable in directions around the longitudinal axis (periaxial directions of the longitudinal axis) with respect to the second sheath section 16. The second sheath section 16 includes a non-bending cylindrical section 18 extended along the longitudinal axis L, and a bending cylindrical section 19 provided to the distal direction side of the non-bending cylindrical section 19 in a bendable manner. Each of bending directions of the bending cylindrical section 19 is perpendicular to the longitudinal axis L. When the bending cylindrical section 19 bends, a bending angle α of the first sheath section 15 with respect to the non-bending cylindrical section 18 varies. That is, the bending angle α between a first central axis C1 and a second central axis C2 varies, the first central axis C1 being coaxial with the longitudinal axis L in the first sheath section 15, and the second central axis C2 being coaxial with the longitudinal axis L in the non-bending cylindrical section 18 of the second sheath section 16.

Figure 5:
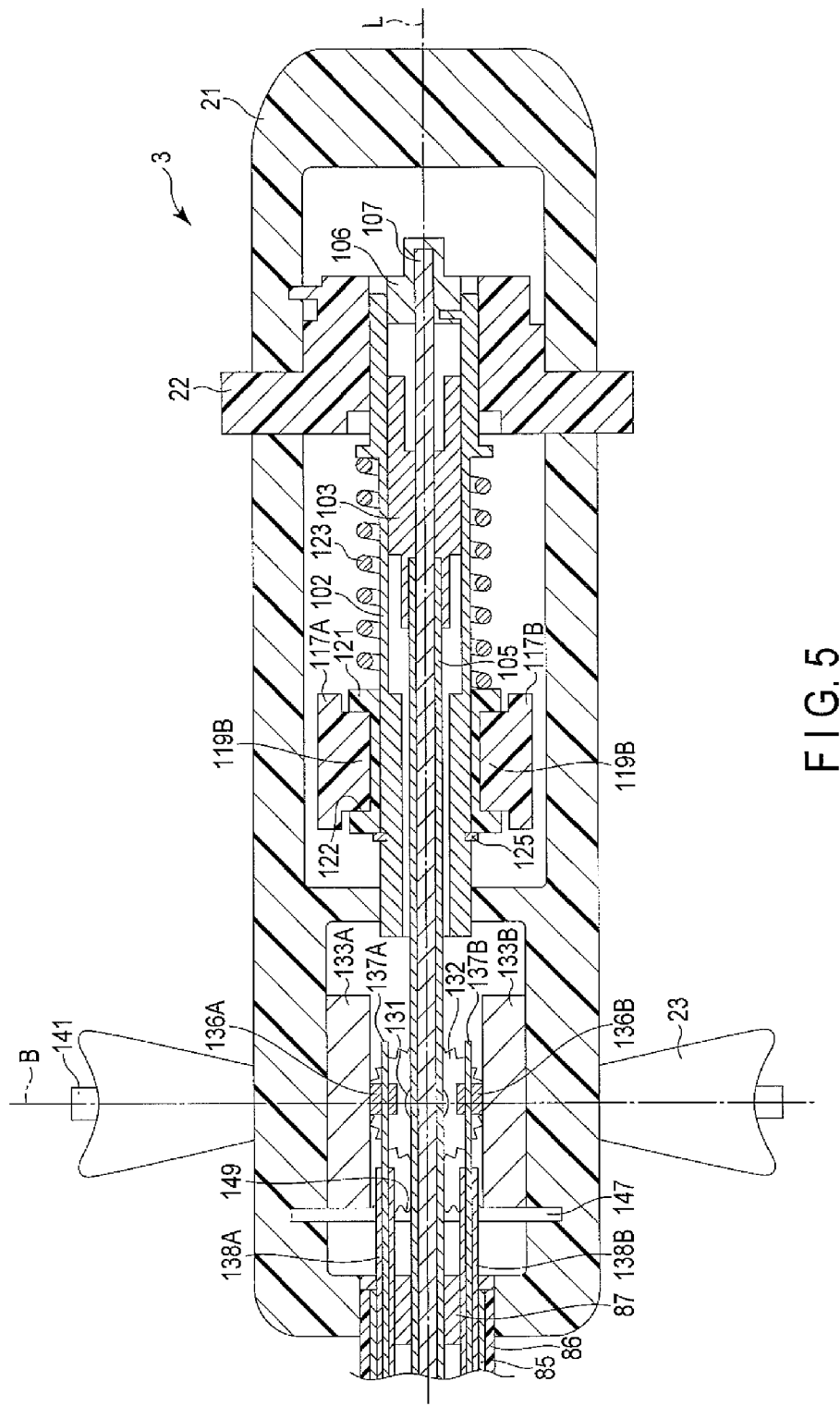
FIG. 5 is a cross-sectional view schematically showing the operation unit according to the first embodiment in a cross-section which runs through the longitudinal axis and which is perpendicular to the rotating axis of the bending operation lever.

FIGS. 4 and 5 are views showing a configuration of the operation unit 3. As shown in FIG. 1A, FIG. 1B, FIG. 4, and FIG. 5, the operation unit 3 is placed to the proximal direction side of the second sheath section 16 of the insertion unit 2. The operation unit 3 includes a cylindrical case 21 extended along the longitudinal axis L. A rotating operation knob 22 as a rotating operating section, which is configured to perform a rotating operation of rotating the grasping section 11 and the first sheath section 15 with respect to the second sheath section 16, is attached to the cylindrical case 21. The rotating operation knob 22 is rotatable in the directions around the longitudinal axis with respect to the cylindrical case 21. Further, a bending operation lever 23 as a bending operating section, which is configured to perform a bending operation of bending the bending cylindrical section 19, is attached to the cylindrical case 21. The bending operation lever 23 is provided to the distal direction side of the rotating operation knob 22. Furthermore, the bending operation lever 23 is rotatable about a rotating axis R, which is perpendicular to the longitudinal axis L, with respect to the cylindrical case 21. The rotating axis R is substantially perpendicular to the bending directions of the bending cylindrical section 19.

The operation unit 3 includes an opening/closing operating section 25 which is configured to carry out an opening/ closing operation of opening or closing the jaw 13 with respect to the probe 12. The opening/closing operating section 25 includes a fixed handle 26 which is extended from the cylindrical case 21 toward a direction away from the longitudinal axis L, and a movable handle 27 which is openable and closable with respect to the fixed handle 26. One end of the cable 5 is connected to the fixed handle 26 at a position away from the cylindrical case 21. The movable handle 27 is placed to the distal direction side of the fixed handle 26, and opening-and-closing directions of the movable handle 27 are substantially parallel to the longitudinal axis L. Therefore, the opening/closing operating section 25 is a pistol-type opening/closing operating section. Furthermore, the bending operation lever 23 is arranged on the same side as the opening/closing operating section 25 with the longitudinal axis L being the center.

As shown in FIG. 2 and FIG. 3, an ultrasonic generating section 32 which includes piezoelectric elements 31 configured to convert a current into ultrasonic vibration is provided in the first sheath section 15. One end of each of electrical wiring lines 33A and 33B is connected to the ultrasonic generating section 32. The other end of each of the electrical wiring lines 33A and 33B is connected to the ultrasonic generation current supply section 7 of the power supply unit 6 through an inside of the insertion unit 2, an inside of the operation unit 3, and an inside of the cable 5. When a current is supplied to the ultrasonic generating section 32 through the electrical wiring lines 33A and 33B, the ultrasonic vibration is generated. A horn 35 is provided to the distal direction side of the ultrasonic generating section 32. An amplitude of the ultrasonic vibration generated in the ultrasonic generating section 32 is increased by the horn 35, and this vibration is transmitted to the probe 12. The ultrasonic generating section 32 and the horn 35 are provided being fixed to the probe 12.

Moreover, one end of an electrical wiring line 37 that is different from the electrical wiring lines 33A and 33B is connected to the ultrasonic generating section 32. The other end of the electrical wiring line 37 is connected to the high-frequency current supply section 8 of the power supply unit 6 through the inside of the insertion unit 2, the inside of the operation unit 3, and the inside of the cable 5. A high-frequency current is supplied from the high-frequency current supply section 8 to the probe 12 through the electrical wiring line 37, the ultrasonic generating section 32, and the horn 35. As a result, the probe 12 functions as a first electrode section.

The first sheath section 15 includes a probe fixed portion 41 which is provided being fixed to the probe 12, and a movable portion 42 which is movable along the longitudinal axis L with respect to the probe fixed portion 41. The probe fixed portion 41 includes a cylindrical member 43 fixed to the horn 35, and a tube member 45 fixed to the proximal direction side of the cylindrical member 43. The ultrasonic generating section 32 is accommodated in the tube member 45. Further, the cylindrical member 43 and the tube member 45 are made of an insulating material. The probe fixed portion 41 includes a joint member 47 fixed to the proximal direction side of the tube member 45, and a slider receiving member 49 fixed to the joint member 47 via a fixing screw 48.

The movable portion 42 includes a movable pipe 51 provided to an outer peripheral direction side of the tube member 45, and a movable tube 52 which covers the movable pipe 51 from the outer peripheral direction side. The movable pipe 51 is made of a conductive material, and the movable tube 52 is made of an insulating material.

Furthermore, the movable section 42 includes a joint member 55 fixed to the proximal direction side of the movable pipe 51 via a fixing screw 53, and a slider member 59 fixed to the joint member 55 via a fixing screw 57. The slider member 59 is coupled to be movable with respect to the slider receiving member 49 along the longitudinal axis L.

Figure 6:
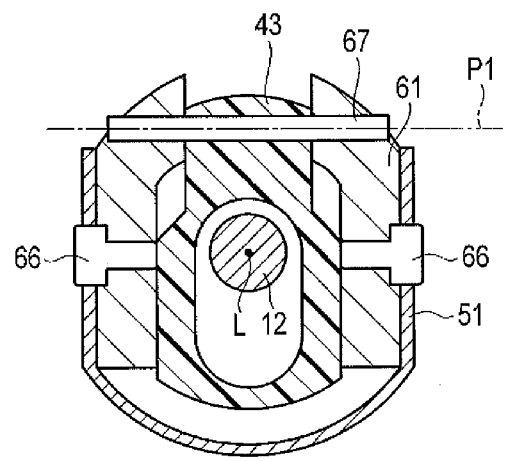
FIG. 6 is a cross-sectional view taken along a line VI-VI in FIG. 2.
Figure 7:
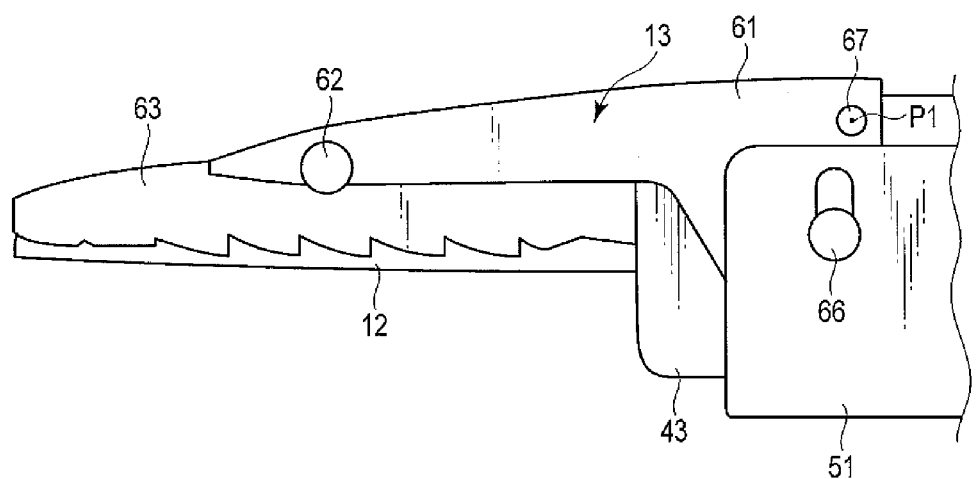
FIG. 7 is a side elevation schematically showing a coupling configuration between a jaw and a first sheath section according to the first embodiment.

FIG. 6 is a cross-sectional view taken along a line VI-VI in FIG. 2. FIG. 7 is a view showing a coupling configuration between the jaw 13 and the first sheath section 15. As shown in FIG. 2, FIG. 6, and FIG. 7, the jaw 13 includes a jaw main body 61 made of a conductive material, an electrode member 63 coupled with the jaw main body 61 via a connection pin 62, and a pad member 65 attached to the electrode member 63. The electrode member 63 is made of a conductive material, and the pad member 65 is made of an insulating material. A distal end portion of the movable pipe 51 of the movable portion 42 of the first sheath section 15 is connected to the jaw main body 61 via a connection screw 66. Further, a distal end portion of the cylindrical member 43 of the probe fixed portion 41 of the first sheath section 15 is attached to the jaw main body 61 via a coupling pin 67. The jaw 13 is rotatable revolve with respect the probe fixed portion 41 with a fulcrum axis P1 being coaxial with the coupling pin 67. As described above, the coupling pin 67 and the jaw main body 61 function as a coupling portion which couples the probe fixed portion 41 with the movable portion 42.

The coupling pin 67 serving as the fulcrum axis 21 of rotating motion (opening/closing) of the jaw 13 is placed to an opening direction side of the jaw 13 compared with connection screw 66 as a connecting portion of the movable portion 42 to the jaw 13. Therefore, when the movable portion 42 of the first sheath section 15 moves toward the proximal direction with respect to the probe fixed portion 41, the jaw 13 closes with respect to the probe 12. On the other hand, when the movable portion 42 of the first sheath section 15 moves toward the distal direction with respect to the probe fixed portion 41, the jaw 13 opens with respect to the probe 12.

The bending cylindrical section 19 of the second sheath section 16 includes an active bending portion 72 formed by coupling bending pieces 73 aligned along the longitudinal axis L, and a bending portion envelope 76 covering the active bending portion from the outer peripheral direction side. Each bending piece 73 is made of a conductive material, and is rotatable with respect to an adjacent bending piece 73. The bending portion envelope 76 is made of an insulating material.

Figure 8:
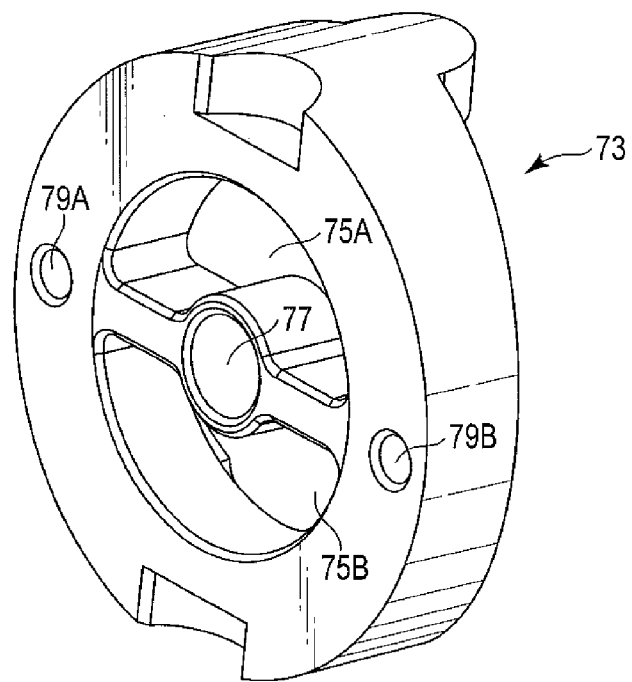
FIG. 8 is a perspective view schematically showing a configuration of a bending piece in a bending cylindrical section according to the first embodiment.

FIG. 8 is a view showing a configuration of the bending piece 73. As shown in FIG. 8, hollow portions (cavity portions) 75A and 75B are provided in each bending piece 73. Electrical wiring lines 43A, 43B, and 47 are extended through the hollow portion 75A or the hollow portion 75B. A hole-shaped portion 77 is formed in each bending piece 73 to be coaxial with the longitudinal axis L. Further, hole-shaped portions 79A and 79B are provided in each bending piece 73 to be parallel to the longitudinal axis L. The hole-shaped portions 79A and 79B are arranged apart from each other at substantially 180° in the periaxial directions of the longitudinal axis.

As shown in FIG. 2 and FIG. 3, a connection tube 81 made of a conductive material is coupled to the distal direction side of the active bending portion 72. The joint member 55 of the movable portion 42 of the first sheath section 15 is coupled to the distal direction side of the connection tube 81. Furthermore, the joint member 55 is coupled with the connection tube 81 to allow its rotating motion in the directions around the longitudinal axis. Moreover, the movable pipe 51 of the movable portion 42 and the connection tube 81 are connected to each other via an electrical connection plate 82 made of a conductive material. The electrical connection plate 82 is rotatable in the periaxial directions of the longitudinal axis with respect to the second sheath section 16 together with the first sheath section 15. The electrical connection plate 82 rotates with respect to the connection tube 81 in a state that the electrical connection plate 82 always (constantly) contacts with the connection tube 81. Therefore, the connection tube 81 and the movable pipe 51 of the movable portion 42 are constantly electrically connected to each other via the electrical connection plate 82.

A connection member 83 is coupled to the proximal direction side of the active bending portion 72. The connection member 83 is made of a conductive material. The non-bending cylindrical section 18 of the second sheath section 16 includes a cylindrical member 85 made of a conductive material, and a tube member 86 covering the cylindrical member 85 from the outer peripheral direction side. The tube member 86 is made of an insulating material. The cylindrical member 85 and the tube member 86 are inserted into the cylindrical case 21 of the operation unit 3.

As shown in FIG. 4 and FIG. 5, an electrical connection member 87 made of a conductive material is fixed to the cylindrical case 21. A proximal end portion of the cylindrical member 85 and a proximal end portion of the tube member 86 are coupled with the electrical connection member 87. One end of an electrical wiring line 89 is connected to the electrical connection member 87. The other end of the electrical wiring line 89 is connected to the high-frequency current supply section 8 of the power supply unit 6 through the inside of the operation unit 3 and the inside of the cable 5. A high-frequency current is supplied from the high-frequency current supply section 8 to the jaw 13 through the electrical wiring line 89, the cylindrical member 85, the connection member 83, the active bending portion 72, the connection tube 81, the electrical connection plate 82, and the movable pipe 51. As a result, the electrical member 63 of the jaw 13 functions as a second electrode section whose electric potential is different from that of the first electrode section.

In the operation unit 3, a button attachment portion 91 is provided between the cylindrical case 21 and the fixed handle 26. The button attachment portion 91 is placed to the distal direction side of the fixed handle 26 and the rotating operation knob 22 and also placed on the proximal direction side of the bending operation lever 23. Additionally, the button attachment portion 91 is arranged on the side where the opening/closing operating section 25 is placed with the longitudinal axis L being the center. A first energy mode input button 92A and a second energy mode input button 92B as energy mode input sections are disposed to the button attachment portion 91. An electrical circuit board 93 is provided in the button attachment portion 91. One end of each of electrical wiring lines 95 and 96 is connected to the electrical circuit board 93. The other end of each of the electrical wiring lines 95 and 96 is connected to the control section 9 in the power supply unit 6 through the inside of the operation unit 3 and the inside of the cable 5.

When the first energy mode input button 92A is pressed, an electrical signal is input to the control section 9 from the electrical circuit board 93 through the electrical wiring line 95. As a result, the control section 9 controls an energy supply state in the first energy mode. In the first energy mode, for example, an electric current is supplied from the ultrasonic generation current supply section 7 to the ultrasonic generating section 32. As a result, ultrasonic vibration is generated in the ultrasonic generating section 32, and the ultrasonic vibration is transmitted to the probe 12. When the second energy mode input button 92B is pressed, an electrical signal is input to the control section 9 from the electrical circuit board 93 through the electrical wiring line 96. As a result, the control section 9 controls an energy supply state in the second energy mode. In the second energy mode, for example, a high-frequency current is supplied from the high-frequency current supply section 8 to the probe 12 and the jaw 13. As a result, the probe 12 is used as the first electrode section, and the electrode member 63 of the jaw 13 is used as the second electrode section, thereby carrying out a bipolar treatment.

Figure 9:
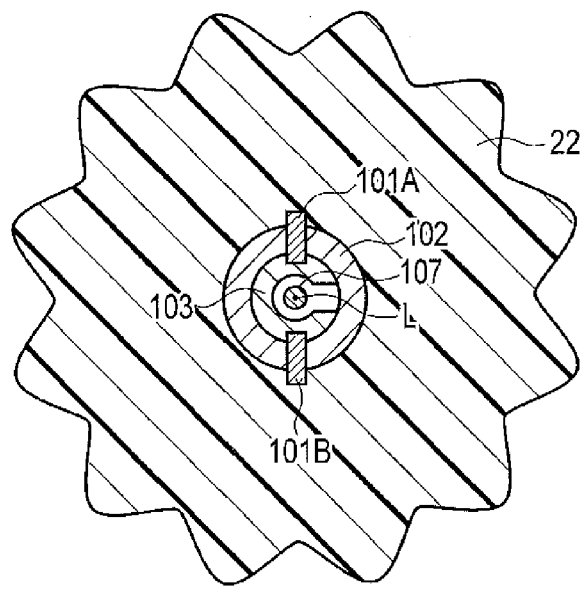
FIG. 9 is a cross-sectional view taken along a line IX-IX in FIG. 4.

FIG. 9 is a cross-sectional view taken along a line IX-IX in FIG. 4. FIG. 10 is a cross-sectional view taken along a line X-X in FIG. 4. Further, FIG. 11 is a cross-sectional view taken along a line 11-11 in FIG. 4. As shown in FIG. 4, FIG. 5, and FIG. 9, a movable cylindrical member 102 and a connection cylindrical member 103 are coupled with the revolving operation knob 22 via engagement pins 101A and 101B. The movable cylindrical member 102 is placed to the inner peripheral direction side of the rotating operation knob 22 and the outer peripheral direction side of the connection cylindrical member 103. The connection cylindrical member 103 is provided being fixed to the rotating operation knob 22. The movable cylindrical member 102 is movable with respect to the rotating operation knob 22 along the longitudinal axis L. However, the rotating motion of the movable cylindrical member 102 with respect to the rotating operation knob 22 in one of the periaxial directions of the longitudinal axis is regulated. Therefore, the movable cylindrical member 102 and the connection cylindrical member 103 is rotatable together with the rotating operation knob 22 in the directions around the longitudinal axis with respect to the cylindrical case 21.

A proximal end of a guide pipe 105 is fixed to the distal direction side of the connection cylindrical member 103. The guide pipe 105 is extended along the longitudinal axis L. Furthermore, as shown in FIG. 4. FIG. 5. and FIG. 10, a proximal end of a drive shaft 107 is fixed to the movable cylindrical member 102 via a joint member 106. The drive shaft 107 is extended along the longitudinal axis L, and inserted into the guide pipe 105. The drive shaft 107 is movable together with the movable cylindrical member 102 with respect to the rotating operation knob 22, the connection cylindrical member 103, and the guide pipe 105 along the longitudinal axis L. Moreover, the guide pipe 105 and the drive shaft 107 are rotatable together with the rotating operation knob 22 with respect to the cylindrical case 21 in the periaxial directions of the longitudinal axis.

As shown in FIG. 2 and FIG. 3, a distal end of the guide pipe 105 and a distal end of the drive shaft 107 are extended to the inside of the non-bending cylindrical section 18 of the second sheath section 16.

In the non-bending cylindrical section 18, a joint member 109 is provided. The joint member 109 is coupled to the proximal direction side of the connection member 83, and is rotatable with respect to the connection member 83 in the directions around the longitudinal axis. A distal end of the guide pipe 105 is fixed to the joint member 109. Therefore, in the non-bending cylindrical section 18, the drive shaft 107 is guided by the guide pipe 105.

Further, a proximal end of a guide coil 111 which is a guide member is fixed to the joint member 109. The guide coil 111 is extended through the inside of the bending cylindrical section 19 along the longitudinal axis L. The guide coil 111 is inserted into the hole-shaped portion 77 in each bending piece 73 of the active bending portion 72. A distal end of the guide coil 111 is connected to the slider receiving member 49 of the probe fixed portion 41 of the first sheath section 15. The guide pipe 105, the joint member 109, and the guide coil 111 are rotatable together with the rotating operation knob 22 with respect to the cylindrical case 21 and the second sheath section 16 in the periaxial directions of the longitudinal axis.

Furthermore, since the guide coil 11 is extended through the bending cylindrical section 19, it has low rigidity. Reducing the rigidity of the guide coil 111 prevents a reduction in bending properties of the bending cylindrical section 19 caused by the guide coil 111. Therefore, the rigidity of the active bending portion 72 is higher than that of the guide coil 111. It is to be noted that, in the active bending portion 72, each bending piece 73 is rotatable (pivotable) with respect to an adjacent bending piece 73. Therefore, even if the active bending portion 72 has the high rigidity, the bending properties of the bending cylindrical section 19 are not reduced. Moreover, since the guide coil 111 has the low rigidity, when acting force acts, the guide coil 111 contracts and deforms.

A proximal end of an opening/closing wire 113 is fixed to a distal end of the drive shaft 107. The opening/closing wire 113 is extended along the longitudinal axis L through an inside of the joint member 109 and an inside of the guide coil 111. In the bending cylindrical section 19, the opening/closing wire 113 is inserted through the guide coil 111, and the opening/closing wire 113 is guided by the guide coil 111. The opening/closing wire 113 is movable together with the drive shaft 107 with respect to the guide pipe 105 and the guide coil 111 along the longitudinal axis L. Additionally, the opening/closing wire 113 and the drive shaft 107 are rotatable together with the rotating operation knob 22 with respect to the cylindrical case 21 and the second sheath section 16 in the directions around the longitudinal axis. A distal end of the opening/closing wire 113 is fixed to the slider member 59 of the movable portion 42 of the first sheath section 15.

When the rotating operation knob 22 is rotated in one of the directions around the longitudinal axis, the connection cylindrical member 103, the guide pipe 105, the joint member 109, and the guide coil 111 rotate with respect to the second sheath section 16 in one of the directions around the longitudinal axis. As a result, the probe fixed portion 41 of the first sheath section 15 rotates with respect to the second sheath section 16 in one of the directions around the longitudinal axis (periaxial direction of the longitudinal axis). Further, the probe 12, the ultrasonic generating section 32, and the horn 35, which are provided in the grasping section 11 with being fixed to the probe fixed portion 41, rotates with respect to the second sheath section 16 in one of the directions around the longitudinal axis. That is, the guide pipe 105 and the guide coil 111 function as a rotating transmitting portion configured to rotate the probe 12 of the grasping section 11 and the probe fixed portion 41 of the first sheath section 15 with respect to the second sheath section 16 in one of the directions around the longitudinal axis by rotating. The guide pipe 105 and the guide coil 111 as the rotating transmitting portion are extended in the second sheath section 16 along the longitudinal axis L. Additionally, the guide pipe 105 and the guide coil 111 rotate by rotating the rotating operation knob 22 in one of the directions around the longitudinal axis.

Further, when the rotating operation knob 22 is rotated in one of the directions around the longitudinal axis, the movable cylindrical member 102, the drive shaft 107, and the opening/closing wire 113 rotate with respect to the second sheath section 16 in one of the directions around the longitudinal axis. As a result, the movable portion 42 of the first sheath section 15 rotates with respect to the second sheath section 16 in one of the directions around the longitudinal axis (periaxial directions of the longitudinal axis). Furthermore, the jaw 13 provided in the grasping section 11 while being coupled with the movable portion 42 rotates with respect to the second sheath section 16 in one of the directions around the longitudinal axis. That is, the drive shaft 107 and the opening/closing wire 113 function as a rotating transmitting portion configured to rotate the jaw 13 of the grasping section 11 and the movable portion 42 of the first sheath section 15 with respect to the second sheath section 16 in one of the directions around the longitudinal axis by rotating. The drive shaft 107 and the opening/closing wire 113 as the rotating transmitting portion are extended in the second sheath section 16 along the longitudinal axis L. Moreover, the drive shaft 107 and the opening/closing wire 113 rotate by rotating the rotating operation knob 22 in the directions around the longitudinal axis. As described above, the grasping section 11 and the first sheath section 15 rotate with respect to the second sheath section 16 in the directions around the longitudinal axis by the rotating operation using the rotating operation knob 22.

As shown in FIG. 4, FIG. 5, and FIG. 11, the movable handle 27 is attached to the cylindrical case 21 via a fulcrum pin 115. The movable handle 27 is rotatable with respect to the cylindrical case 21 with the fulcrum pin 115 being a fulcrum axis P2. Additionally, the movable handle 27 includes arm portions 117A and 117B. An engagement protrusion 119A protruding toward the inner peripheral direction is provided to the arm portion 117A, and an engagement protrusion 119B protruding toward the inner peripheral direction is provided to the arm portion 117B.

A slide member 121 is arranged to the outer peripheral direction side of the movable cylindrical member 102. An engagement groove 122 that is concaved in the inner peripheral direction is formed in the slide member 121 along the periaxial directions of the longitudinal axis. When the engagement protrusions 119A and 119B engage with the engagement groove 122, the movable handle 27 is attached to the slide member 121. The slide member 121 is rotatable together with the movable cylindrical member 102 with respect to the movable handle 27 and the cylindrical case 21 in the periaxial directions of the longitudinal axis. The slide member 121 is made of an insulating material. Therefore, the movable cylindrical member 102 is electrically insulated from the movable handle 27.

Additionally, a coil spring 123 as an elastic member and a stopper 125 are provided to the outer peripheral direction side of the movable cylindrical member 102. One end of the coil spring 123 is connected to a proximal end of the slide member 121, and the other end of the same is connected to the movable cylindrical member 102. When the jaw 13 does not come into contact with a grasping target such as a biological tissue (body tissue), the coil spring 123 is extended between the movable cylindrical member 102 and the slide member 121 in a reference state where the coil spring 123 is contracted by a displacement amount x0 from a natural state. Further, movement of the slide member 121 toward the distal direction is regulated by the stopper 125.

In a case of grasping a grasping target between the probe 12 and the jaw 13, the movable handle 27 is closed with respect to the fixed handle 26. As a result, the movable handle 27 rotates about the fulcrum shaft P2, and the slide member 121 and the movable cylindrical member 102 move with respect to the rotating operation knob 22 and the connection cylindrical member 103 toward the proximal direction along the longitudinal axis L. At this time, the coil spring 123 does not contract from the reference state.

When the movable cylindrical member 102 moves toward the proximal direction, the drive shaft 107 and the opening/closing wire 113 move with respect to the connection cylindrical member 103, the guide pipe 105, and the guide coil 111 toward the proximal direction. That is, the drive shaft 107 and the opening/closing wire 113 are pulled toward the proximal direction along the longitudinal axis L. When the opening/closing wire 113 is pulled toward the proximal direction, the movable portion 42 of the first sheath section 15, to which the distal end of the opening/closing wire 113 is fixed, moves with respect to the probe fixed portion 41 toward the proximal direction. When the movable portion 42 of the first sheath section 15 moves with respect to the probe fixed portion 41 toward the proximal direction, the jaw 13 closes with respect to the probe 12.

Furthermore, when the jaw 13 has come into contact with the grasping target, e.g., a biological tissue, the closing motion of the jaw 13 temporarily stops. Therefore, the movement of the movable cylindrical member 102, the drive shaft 107, and the opening/closing wire 113 toward the proximal direction temporarily stops. In this state, when the movable handle 27 is further closed with respect to the fixed handle 26, the slide member 121 moves toward the proximal direction with respect to the movable cylindrical member 102. The movement of the slide member 121 relative to the movable cylindrical member 102 allows the coil spring 123 to further contract from the reference state. As a result, each of grasping targets having various thicknesses or shapes can be grasped with a substantially constant grasping force.

When the movable handle 27 is opened with respect to the fixed handle 26 from the state in which the grasping target is grasped between the jaw 13 and the probe 12, the slide member 121 moves with respect to the movable cylindrical member 102 toward the distal direction. As a result, the coil spring 123 stretches (elongates) and becomes the reference state.

Furthermore, the slide member 121 and the movable cylindrical member 102 move with respect to the revolving operation knob 22 and the connection cylindrical member 103 along the longitudinal axis L toward the distal direction. When the movable cylindrical member 102 moves toward the distal direction, the drive shaft 107 and the opening/closing wire 113 move toward the distal direction with respect to the connection cylindrical member 103, the guide pipe 105, and the guide coil 111. When the opening/closing wire 113 moves toward the distal direction, the movable portion 42 of the first sheath section 15, to which the distal end of the opening/closing wire 113 is fixed, moves with respect to the probe fixed portion 41 toward the distal direction. When the movable portion 42 of the first sheath section 15 moves with respect to the probe fixed portion 41 toward the distal direction, the jaw 13 opens with respect to the probe 12.

As described above, the drive shaft 107 and the opening/closing wire 113 are opening/closing transmitting portion configured to open or close the jaw 13 with respect to the probe 12 when they move along the longitudinal axis L. When the opening/closing transmitting portion (107, 113) is pulled toward the proximal direction, the movable portion 42 of the first sheath section 15 moves toward the proximal direction with respect to the probe fixed portion 41. Moreover, the drive shaft 107 and the opening/closing wire 113 are extended in the second sheath section 16 along the longitudinal axis L.

FIG. 12 is a view showing a configuration of the coupling portion between the first sheath section 15 and the second sheath section 16. As shown in FIG. 2, FIG. 3, and FIG. 12, in the bending cylindrical section 19 of the second sheath section 16, an acting force transmitting portion 127 is coupled with the active bending portion 72 via the connection tube 81. The acting force transmitting portion 127 has a rigidity higher than that of the guide coil 111, and is fixed to the connection tube 81. The slider receiving member 49 of the probe fixed portion 41 of the first sheath section 15 is coupled to the distal direction side of the acting force transmitting portion 127. Since the acting force transmitting portion 127 is fixed to the connection tube 81 of the second sheath section 16, the probe fixed portion 41 is rotatable with respect to the acting force transmitting portion 127 in the directions around the longitudinal axis. Moreover, irrespective of the rotating state of the grasping section 11 and the first sheath section 15 relative to the second sheath section 16, the acting force transmitting portion 127 always (constantly) abuts on the slider receiving member 49 of the probe fixed portion 41.

In a state that the movable portion 42 moves with respect to the probe fixed portion 41 toward the proximal direction and the jaw 13 closes with respect to the probe 12, the acting force acting toward the proximal direction acts on the probe fixed portion 41 from the movable portion 42 through the coupling portion (the coupling pin 67 and the jaw main body 61). Since the acting force transmitting portion 127 constantly abuts on the slider receiving member 49 of the probe fixed portion 41, the acting force acting on the probe fixed portion 41 is transmitted to the acting force transmitting portion 127. Additionally, the acting force acting toward the proximal direction is transmitted from the acting force transmitting portion 127 to the active bending portion 72 of the bending cylindrical section 19 through the connection tube 81. Since the active bending portion 72 has the high rigidity, even if the acting force acts, the active bending portion 72 does not deform.

FIG. 13 is a cross-sectional view taken along a line 13-13 in FIG. 4, and FIG. 14 is a cross-sectional view taken along a line 14-14 in FIG. 13. As shown in FIG. 4, FIG. 5, and FIG. 13, the bending operation lever 23 is coupled with a shaft member 131. The shaft member 131 is fixed to a pinion gear 132 in the cylindrical case 21. The shaft member 131 and the pinion gear 132 are rotatable about a rotating axis R together with the bending operation lever 23.

Rack members 133A and 133B are attached to the cylindrical case 21. The rack members 133A and 133B are movable with respect to the cylindrical case 21 along the longitudinal axis L. As shown in FIG. 14, a gear portion 135A is provided to the rack member 133A, and a gear portion 135B is provided to the rack member 133B. The gear portions 135A and 135B mesh with the pinion gear 132. When the pinion gear 132 rotates about the rotary axis R, the rack members 133A and 1332 move with respect to the cylindrical case 21 along the longitudinal axis L.

As shown in FIG. 13, a connection member 136A is fixed to the rack member 133A. Further, a proximal end of a bending wire 137A as a bending transmitting portion is connected to the connection member 136A. As shown in FIG. 3, the bending wire 137A is extended through the inside of the second sheath section 16 along the longitudinal axis L. A guide member 138A through which the bending wire 137A is inserted is extended inside the non-bending cylindrical section 18 along the longitudinal axis L. A distal end of the guide member 138A is fixed to the connection member 83, and a proximal end of the same is fixed to the cylindrical case 21. In the non-bending cylindrical section 18, the bending wire 137A is guided by the guide member 138A. In each bending piece 73 of the active bending portion 72, the bending wire 137A is inserted through the hole-shaped portion 79A. A distal end of the bending wire 137A is connected to the connection tube 81 of the second sheath section 16.

Furthermore, as shown in FIG. 13, a connection member 136B is fixed to the rack member 1333. Moreover, a proximal end of the bending wire 137B as the bending transmitting portion is connected to the connection member 136B. As shown in FIG. 3, the bending wire 137B is extended in the second sheath section 16 along the longitudinal axis L. In the non-bending cylindrical section 18, a guide member 138B though which the bending wire 137B is inserted is extended along the longitudinal axis L. A distal end of the guide member 1385 is fixed to the connection member 83, and a proximal end of the same is fixed to the cylindrical case 21. In the non-bending cylindrical section 18, the bending wire 137B is guided by the guide member 138B. Moreover, in each bending piece 73 of the active bending portion 72, the bending wire 137B is inserted through the hole-shaped portion 79B. A distal end of the bending wire 137B is connected to the connection tube 81 of the second sheath section 16.

When the bending operation lever 23 is rotated about the rotating axis R in one of rotating directions, the pinion gear 132 rotates integrally with the bending operation lever 23. As a result, the rack member 133A and the connection member 136A move with respect to the cylindrical case 21 toward the proximal direction, and the bending wire 137A is pulled toward the proximal direction. When the bending wire 137A is pulled, the active bending portion 72 actively bends in one of bending directions. On the other hand, when the bending operation lever 23 is rotated about the rotating axis R in the other of the rotating directions, the pinion gear 132 rotates integrally with the bending operation lever 23. As a result, the rack member 133B and the connection member 136B move with respect to the cylindrical case 21 toward the proximal direction, and the bending wire 137B is pulled toward the proximal direction. When the bending wire 1372 is pulled, the active bending portion 72 actively bends in the other of the bending directions.

As described above, the bending wires 137A and 1372 as the bending transmitting portion move along the longitudinal axis L by the bending operation using the bending operation lever 23. That is, when the bending operation lever 23 rotates about the rotating axis R, the bending wires 137A and 137B move along the longitudinal axis L. As a result, the active bending portion 72 actively bends, and the bending cylindrical section 19 is bent.

As shown in FIG. 4 and FIG. 5, a bending lock operation bar 141 as a bending lock operating section is attached to the bending operation lever 23. The bending lock operating bar 141 is configured to perform a bending lock operation. Based on the bending lock operation, the bent state of the bending cylindrical section 19 is locked, and the bent state of the bending cylindrical section 19 is unlocked. The bending lock operation bar 141 has a bar axis B, and is movable along the bar axis B with respect to the bending operation lever 23. The bar axis B is substantially perpendicular to the longitudinal axis L and orthogonal to the rotating axis R of the bending operation lever 23.

Figure 16:
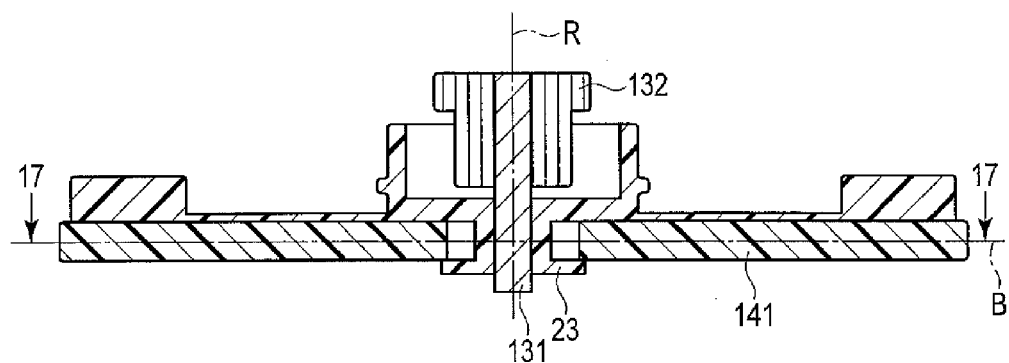
FIG. 16 is a cross-sectional view taken along a line 16-16 in FIG. 15.
Figure 17:
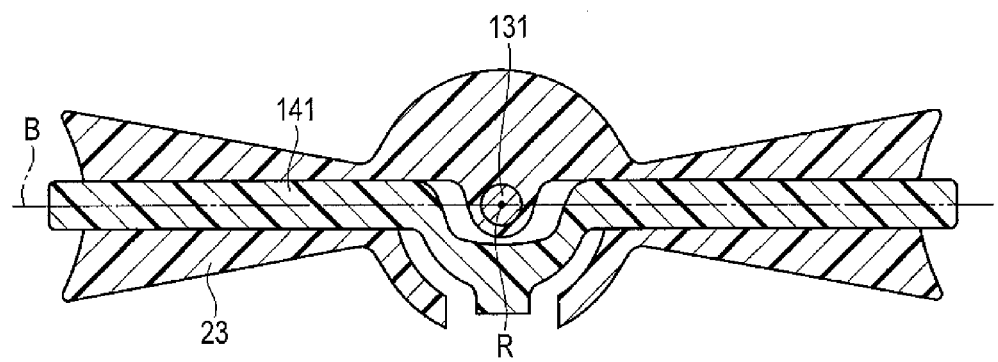
FIG. 17 is a cross-sectional view taken along a line 17-17 in FIG. 16.

FIG. 15 is a view showing a configuration of the bending operation lever 23, the pinion gear 132, and the bending lock operation bar 141. FIG. 16 is a cross-sectional view taken along a line 16-16 in FIG. 15, and FIG. 17 is a cross-sectional view taken along a line 17-17 in FIG. 16. As shown in FIG. 4 and FIG. 15 to FIG. 17, the bending lock operation bar 141 is provided to be inserted into the bending operation lever 23. The bending lock operation bar 141 is rotatable about the rotating axis R integrally with the bending operation lever 23. Further, a lock member 142 is attached to the bending lock operation bar 141. The lock member 142 is placed to the distal direction side of the pinion gear 132, and arranged at a position closer to the longitudinal axis L than the bending lock operation bar 141. The lock member 142 is rotatable about the rotating axis R integrally with the bending operation lever 23.

Figure 18C:
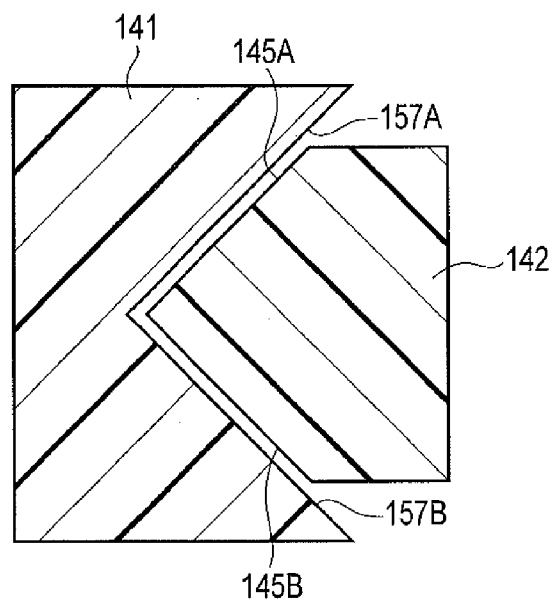
FIG. 18C is a cross-sectional view taken along a line 18C-18C in FIG. 18A.
Figure 19:
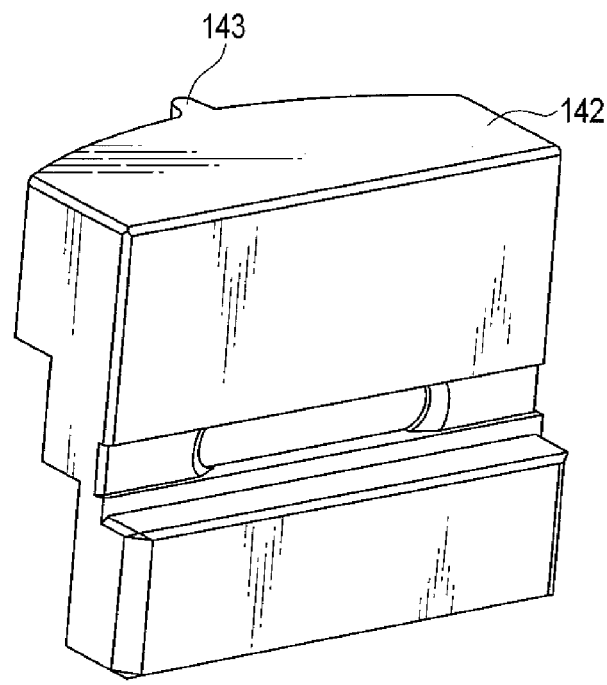
FIG. 19 is a perspective view schematically showing a configuration of a lock member according to the first embodiment.

FIG. 18A is a view showing a configuration near the bending operation lever 23 of the cylindrical case 21. FIG. 18B is a cross-sectional view taken along a line 18B-18B in FIG. 18A, and FIG. 18C is a cross-sectional view taken along a line 180-18C in FIG. 18A. Furthermore, FIG. 19 is a view showing a configuration of the lock member 142. As shown in FIG. 15 and FIG. 18A to FIG. 19, the lock member 142 includes a protruding portion 143 protruding toward a direction away from the rotating axis R. A protruding direction of the protruding portion 143 is perpendicular to the bar axis B.

As shown in FIG. 18A and FIG. 18B, a frame member 147 is fixed to the cylindrical case 21. Groove-shaped portions 149 are formed to the frame member 147 along the periaxial directions of the rotating axis R (directions around the rotating axis R). Moreover, a torsion spring 152 which is a biasing member is provided in the bending operation lever 23. A biasing force acts on the lock member 142 toward the direction away from the rotating axis R by the torsion spring 152.

In a state that a force parallel to the bar axis does not act on the bending lock operation bar 141, the bending lock operation bar 141 does not move with respect to the bending operation lever 23. Therefore, the force does not act on the lock member 142 from the bending lock operation bar 141. Therefore, the lock member 142 is biased toward the direction away from the rotating axis R by the biasing force from the torsion spring 152, and the protruding portion 143 of the lock member 142 engages with one of the groove-shaped portions 149. As a result, the rotating motion of the lock member 142 with the rotating axis R being the center is regulated, and the rotating motion of the pinion gear 132 with the rotating axis R being the center is regulated. When the rotating motion of the pinion gear 132 is regulated, the movement of the rack members 133A and 133B along the longitudinal axis L is regulated, and the movement of the bending wires 137A and 137B along the longitudinal axis L is regulated. As a result, the bent state of the bending cylindrical section 19 is locked.

As shown in FIG. 18A and FIG. 18G, bar side inclined surfaces 157A and 157B are provided to the bending lock operation bar 141. The bar side inclined surfaces 157A and 157B are arranged at positions farther from the longitudinal axis L than the frame member 147. Additionally, lock side inclined surfaces 145A and 145B are provided to the lock member 142. The lock side inclined surface 145A faces the bar side inclined surface 157A, and the lock side inclined surface 145B faces the bar side inclined surface 157B.

When the bending lock operation bar 141 is pressed toward the rotating axis R, the force parallel to the bar axis B acts on the bending lock operation bar 141. As a result, the bending lock operation bar 141 moves with respect to the bending operation lever 23 along the bar axis B. When the bending lock operation bar 141 moves, the lock side inclined surface 145A is pressed by the bar side inclined surface 157A, or the lock side inclined surface 145B is pressed by the bar side inclined surface 157B. As a result, an acting force in a direction toward the rotating axis R acts on the lock member 142. When the acting force acts, the lock member 142 moves toward the rotating axis R against the biasing force from the torsion spring 152. As a result, the protruding portion 143 and the groove-shaped portion 149 are disengaged from each other.

When the protruding portion 143 and the groove-shaped portion 149 are disengaged from each other, the regulation of the rotating motion of the lock member 142 about the rotating axis R is canceled, and the regulation of the rotating motion of the pinion gear 132 about the revolving axis R is canceled (released). When the regulation of the rotating motion of the pinion gear 132 is canceled, the regulation of the movement of the rack members 133A and 133B along the longitudinal axis L is canceled, and the regulation of the movement of the bending wires 137A and 137B is canceled. As a result, the bent state of the bending cylindrical section 19 is unlocked.

Figure 20:
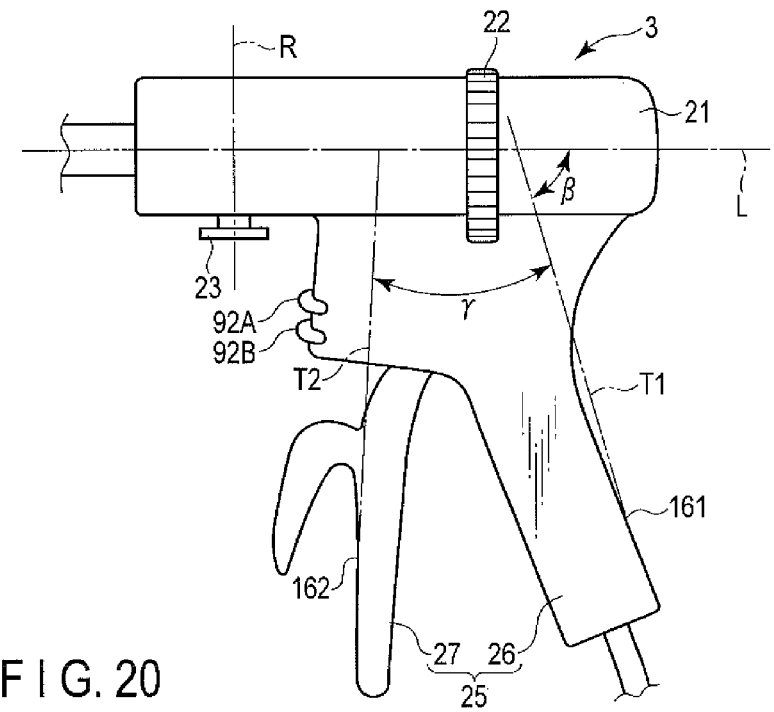
FIG. 20 is a schematic view showing the operation unit in a state that a movable handle is positioned most-opened position with respect to a fixed handle according to the first embodiment.

FIG. 20 is a view showing the operation unit 3 in a state that the movable handle 27 is positioned most-opened position with respect to the fixed handle 26. As shown in FIG. 20, the fixed handle 26 includes a fixed side holding portion 161 which is configured to be held in the opening/closing operation of the jaw 13. The fixed side holding portion 161 forms a proximal end of the fixed handle 26. Additionally, on a reference plane which is parallel to the longitudinal axis L and also parallel to the rotating axis R of the bending operation lever 23, an absolute angle of the fixed side holding portion 161 relative to the proximal direction which is one of directions parallel to the longitudinal axis L is β. The absolute angle β is not smaller than 45° and not greater than 90°.

Further, the movable handle 27 includes a movable side holding portion 162 which is configured to be held in the opening/closing operation of the jaw 13. In the closing operation of the movable handle 27 relative to the fixed handle 26, a pressing force acts on the movable side holding portion 162 toward the proximal direction. Furthermore, on a reference plane which is parallel to the longitudinal axis L and also parallel to the rotating axis R of the bending operation lever 23, at a position where the movable handle 27 is opened at a maximum with respect to the fixed handle 26, a relative angle of the movable side holding portion 162 relative to the fixed side holding portion 161 is γ. The relative angle γ is not smaller than 0° and not greater than 30°, and more preferably not smaller than 0° and not greater than 16°.

Moreover, a first extension line T1 extending from the fixed side holding portion 161 toward the cylindrical case 21 and a second extension line T2 extending from the movable side holding portion 162 toward the cylindrical case 21 are defined. On a reference plane that is parallel to the longitudinal axis L and also parallel to the rotating axis R of the bending operation lever 23, the rotating operation knob 22 is placed in the range between the first extension line T1 and the second extension line T2.

Figure 21:
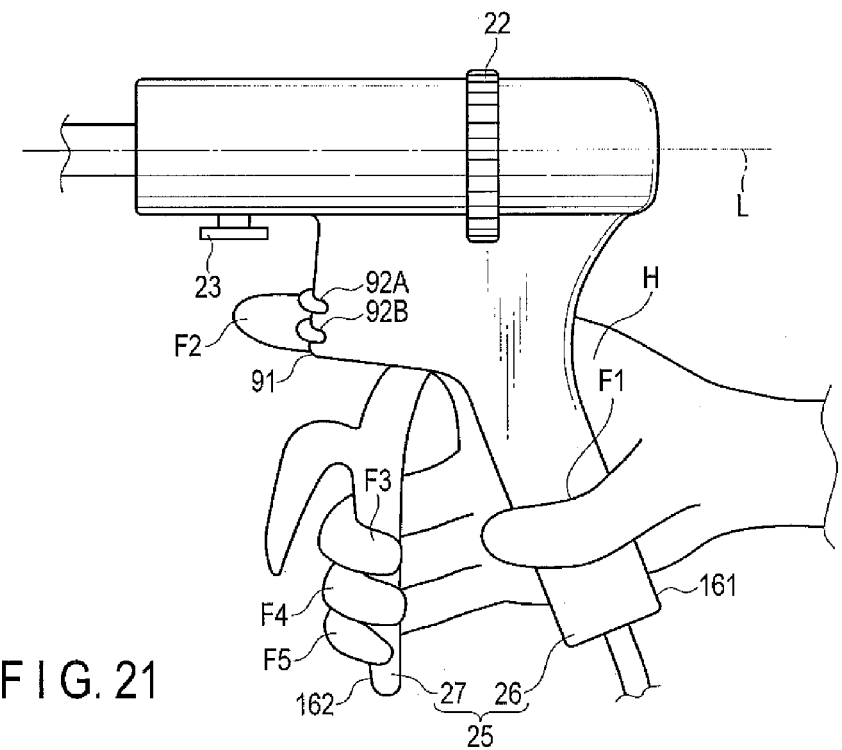
FIG. 21 is a schematic view showing a state in which the operation unit according to the first embodiment is held.

A function of the grasping treatment device 1 will now be described. FIG. 21 is a view showing a state that the operation unit 3 is held. As shown in FIG. 21, when the operation unit 3 is held and the opening/closing operation of the jaw 13 is performed, the fixed side holding portion 161 of the fixed handle 26 is held with a thumb F1 and a palm H. Furthermore, the movable side holding portion 162 of the movable handle 26 is held with a middle finger F3, a ring finger F4, and a little finger F5. Moreover, the index finger F2 is used to perform the bending operation in the bending operation lever 23 and operation input in the first energy mode input button 92A and the second energy mode input button 92B, and the thumb F1 is used to perform the rotating operation in the rotating operation knob 22.

In this embodiment, the absolute angle β of the fixed side holding portion 161 relative to the proximal direction is not smaller than 45° and not greater than 90°. In this case, when the relative angle γ of the movable side holding portion 162 relative to the fixed side holding portion 161 at a position where the movable handle 27 is most-opened with respect to the fixed handle 26 is set to be not smaller than 0° and not greater than 30°, the opening/closing motion of the movable handle 27 relative to the fixed handle 26 can be facilitated. Therefore, the opening/closing operation of the jaw 13 can be facilitated. Moreover, when the relative angle γ of the movable side holding portion 162 relative to the fixed side holding portion 161 at a position where the movable handle 27 is most-opened with respect to the fixed handle 26 is set to be not smaller than 0° and not greater than 16°, the opening/closing motion of the movable handle 27 relative to the fixed handle 26 can be further facilitated. Therefore, the opening/closing operation of the jaw 13 can be further facilitated.

Additionally, in the grasping treatment device 1, the grasping section 11 and the first sheath section 15 located to the distal direction side of the second sheath section 16 are rotatable in the periaxial directions of the longitudinal axis with respect to the second sheath section 16 including the bendable bending cylindrical section 19. To realize such a grasping treatment device 1 without complicating the configuration, the rotating transmitting portion including the guide coil 111, the opening/closing wire 113, and others must be extended in the second sheath section 16 along the longitudinal axis L. In this case, in the operation unit 3, the bending operation lever 23 as the bending operating section must be provided to the distal direction side of the rotating operation knob 22 which is the rotating operating section.

In this embodiment, the rotating operation knob 22 is placed in the range between the first extension line T1 extending from the fixed side holding portion 161 toward the cylindrical case 21 and the second extension line T2 extending from the movable side holding portion 162 toward the cylindrical case 21. In a configuration that the absolute angle β of the fixed side holding portion 161 and the relative angle γ of the movable side holding portion 162 fall in the above-described range and the bending operation lever 23 is placed to the distal direction side of the rotating operation knob 22, placing the rotating operation knob 22 in the range between the first extension line T1 and the second extension line T2 facilitates the rotating motion of the rotating operation knob 22 with use of the thumb F1. Therefore, the rotating operation of rotating the grasping section 11 and the first sheath section 15 with respect to the second sheath section 16 can be easily performed.

Further, the bending operation lever 23 and the button attachment portion 91 are arranged on the side where the opening/closing operating section 25 is placed with the longitudinal axis L being the center. Therefore, in a state that the fixed handle 26 and the movable handle 27 are held, rotating the bending operation lever 23 and pressing the first energy mode input button 92A and the second energy mode input button 923 can be easily carried out. Therefore, in a state that the fixed handle 26 and the movable handle 27 are held, the bending operation of bending the bending cylindrical section 19 and the energy mode switching can be easily carried out.

Furthermore, in the grasping treatment device 1, when the protruding portion 143 of the lock member 142 engages with any one of the groove-shaped portions 149, the bent state of the bending cylindrical section 19 is locked as described above. In a case of unlocking the bent state of the bending cylindrical section 19, the bending lock operation bar 141 is pressed toward the rotating axis R. As a result, the bent state of the bending cylindrical section 19 is unlocked as described above. Here, since the bent state is unlocked by pressing the bending lock operation bar 141 attached to the bending operation bar 23, the bent state of the bending cylindrical section 19 can be easily unlocked.

Moreover, since the bent state is unlocked, the regulation of the rotating motion of the pinion gear 132 about the rotating axis R can be canceled. Therefore, the pinion gear 132 can be rotated without applying a large force to the bending operation lever 23. That is, the bending cylindrical section 19 can be bent without applying the large force to the bending operation lever 23. As a result, the bending operation of bending the bending cylindrical section 19 can be further easily conducted.

Additionally, at the time of grasping a grasping target between the probe 12 and the jaw 13, the movable handle 27 is closed with respect to the fixed handle 26. As a result, the movable cylindrical member 102 moves with respect to the rotating operation knob 22 and the connection cylindrical member 103 along the longitudinal axis L toward the proximal direction as described above. When the movable cylindrical member 102 moves toward the proximal direction, the drive shaft 107 and the opening/closing wire 113 move toward the proximal direction with respect to the connection cylindrical member 103, the guide pipe 105, and the guide coil 111. When the opening/closing wire 113 is pulled toward the proximal direction, the movable portion 42 of the first sheath section 15 to which the distal end of the opening/closing wire 113 is fixed moves with respect to the probe fixed portion 41 toward the proximal direction. When the movable portion 42 of the first sheath section 15 moves with respect to the probe fixed portion 41 toward the proximal direction, the jaw 13 closes with respect to the probe 12.

In a state that the movable portion 42 moves with respect to the probe fixed portion 41 toward the proximal direction and the jaw 13 closes with respect to the probe 12, the acting force toward the proximal direction acts on the probe fixed portion 41 from the movable portion 42 through the coupling portion (the coupling pin 67 and the jaw main body 61). Since the acting force transmitting portion 127 constantly (always) abuts on the slider receiving member 49 of the probe fixed portion 41, the acting force acting on the probe fixed portion 41 is transmitted to the acting force transmitting portion 127. Further, the acting force toward the proximal direction is transmitted from the acting force transmitting portion 127 to the active bending portion 72 of the bending cylindrical section 19 through the connection tube 81. Since the active bending portion 72 has high rigidity, even if the acting force acts, the active bending portion 72 does not deform.

Since the active bending portion 72 does not deform, the probe fixed portion 41 is firmly fixed to the probe 12. Therefore, in a state that the acting force toward the proximal direction acts on the probe fixed portion 41 from the movable portion 42, the movement of the probe fixed portion 41 due to the acting force can be effectively avoided. In the grasping treatment device 1, since the probe fixed portion 41 is firmly fixed with respect to the probe 12, a grasping target is grasped with appropriate grasping force when the movable portion 42 moves with respect to the probe fixed portion 41. Therefore, since the movement of the probe fixed portion 41 due to the acting force is avoided, the grasping target can be grasped with the appropriate grasping force.

Therefore, the grasping treatment device 1 having the above-described configuration exercises the following effect. That is, in the grasping treatment device 1, the movable portion 42 moves with respect to the probe fixed portion 41 toward the proximal direction, and the jaw 13 closes with respect to the probe 12. At this time, the acting force functioning toward the proximal direction acts on the probe fixed portion 41 from the movable portion 42 through the coupling portion (the coupling pin 67 and the jaw main body 61). Furthermore, the acting force toward the proximal direction acting on the probe fixed portion 41 is transmitted to the active bending portion 72 of the bending cylindrical section 19 by the acting force transmitting portion 127. Since the active bending portion 72 has high rigidity, even if the acting force acts, the active bending portion 72 does not deform. Since the active bending portion 72 does not deform, the probe fixed portion 41 is firmly fixed to the probe 12. Therefore, in a state that the acting force toward the proximal direction acts on the probe fixed portion 41 from the movable portion 42, the movement of the probe fixed portion 41 due to the acting force can be effectively avoided. When the movement of the probe fixed portion 41 due to the acting force is avoided, a grasping target can be grasped with appropriate force.

(Modification)

Figure 22:
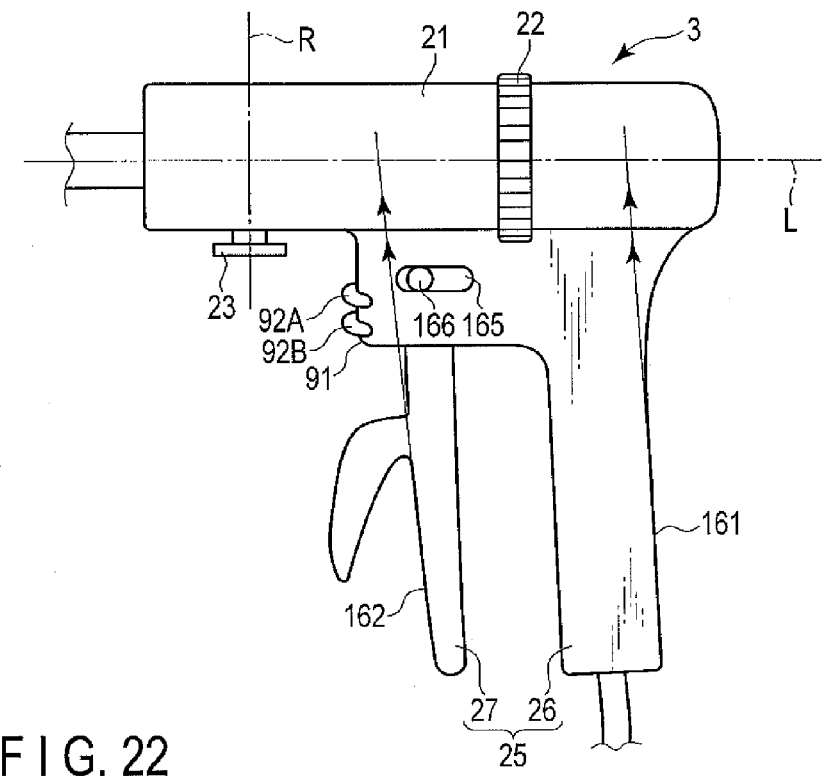
FIG. 22 is a schematic view showing an operation unit according to a first modification.

It is to be noted that the movable handle 27 is rotatable with respect to the cylindrical case 21 with the fulcrum pin 115 being used as the fulcrum shaft P2, but the present invention is not restricted thereto. For example, as shown in FIG. 22 as a first modification, the movable handle 27 may be attached to the cylindrical case 21 to be movable along the longitudinal axis L. In this modification, a slot-shaped slide hole 165 is formed in the cylindrical case 21. Further, in addition to the engagement protrusions 119A and 119B, an engagement protrusion 166 that engages with the slide hole 165 is provided to the movable handle 27. The engagement protrusion 166 is movable in the slide hole 165 along the longitudinal axis L. As a result, when the movable handle 27 closes with respect to the fixed handle 26, the jaw 13 closes with respect to the probe 12 like the first embodiment.

Further, in this modification, at a position where the movable handle 27 is most-opened relative to the fixed handle 26, the relative angle γ of the movable side holding portion 162 relative to the fixed side holding portion 161 is 0°. That is, the movable side holding portion 162 is parallel to the fixed side holding portion 161. Furthermore, at a position where the movable handle 27 is most-closed relative to the fixed handle 26, the movable side holding portion 162 is parallel to the fixed side holding portion 161.

Figure 23:
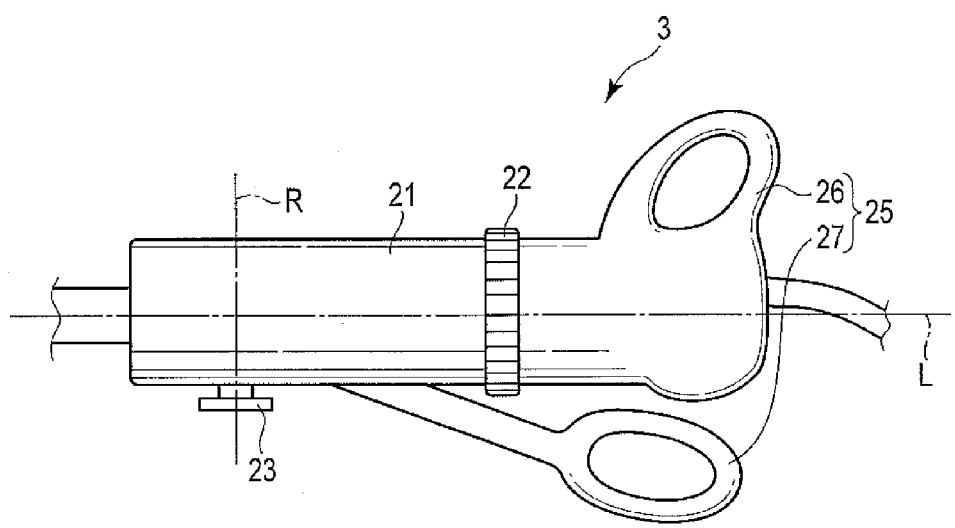
FIG. 23 is a schematic view showing an operation unit according to a second modification.

Moreover, in the first embodiment, the opening/closing directions of the movable handle 27 are substantially parallel to the longitudinal axis L, but the present invention is not restricted thereto. For example, as shown in FIG. 23 as a second modification, the opening/closing directions of the movable handle 27 may be substantially perpendicular to the longitudinal axis L. In this modification, the opening/closing directions of the movable handle 27 are substantially parallel to the rotating axis R of the bending operation lever 23. In this modification, like the first embodiment, when the movable handle 27 closes with respect to the fixed handle 26, the movable cylindrical member 102 moves toward the proximal direction. Consequently, as described above, the jaw 13 closes with respect to the probe 12. Additionally, in this modification, like the first embodiment, the bending operation lever 23 is placed to the distal direction side of the rotating operation knob 22.

Based on the above description, it is sufficient to enable the grasping section 11 and the first sheath section 15 located to the distal direction side of the second sheath section 16 to rotate in the periaxial directions of the longitudinal axis with respect to the second sheath section 16 including the bendable bending cylindrical section 19. Further, in the second sheath section 16, extending the rotating transmitting portion (the guide pipe 105, the drive shaft 107, the guide coil 111, and the opening/closing wire 113) along the longitudinal axis L can suffice. Additionally, it is sufficient to enable the jaw 13 to be opened or closed with respect to the probe 12 in response to the movement of the opening/closing wire 113 as the opening/closing transmitting portion along the longitudinal axis L. In this case, when the opening/closing wire 113 is pulled toward the proximal direction, the movable portion 42 moves toward the proximal direction with respect to the probe fixed portion 41 in the first sheath section 15, and the jaw 13 closes with respect to the probe 12. When the jaw 13 closes with respect to the probe 12, the acting force toward the proximal direction acts on the probe fixed portion 41 from the movable portion 42. The acting force that has acted on the probe fixed portion 41 is transmitted to the bending cylindrical section 19 by the acting force transmitting portion 127.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment device comprising:
   a grasping section which includes a probe extended along a longitudinal axis, and a jaw which is openable/closeable with respect to the probe;
   a first sheath section which is extended to a proximal direction side of the grasping section along the longitudinal axis, the first sheath section including a probe fixed portion that is fixed to the probe, and a movable portion which is connected to the jaw and which is movable with respect to the probe fixed portion along the longitudinal axis;
   a second sheath section which is provided to the proximal direction side of the first sheath section, the second sheath section including a non-bending cylindrical section which is extended along the longitudinal axis, and a bending cylindrical section which is provided to a distal direction side of the non-bending cylindrical section and which is configured to bend to change a bending angle of the first sheath section relative to the non-bending cylindrical section;
   a rotating transmitting portion which is extended in the second sheath section along the longitudinal axis, and which is configured to rotate to allow the grasping section and the first sheath section to rotate in one of periaxial directions of the longitudinal axis with respect to the second sheath section;
   an opening/closing transmitting portion which is extended in the second sheath section along the longitudinal axis, and which is configured to move along the longitudinal axis to enable the jaw to be opened and closed with respect to the probe, the opening/closing transmitting portion being configured to move the movable portion toward the proximal direction with respect to the probe fixed portion by being pulled toward the proximal direction;
   a guide member which is provided in the bending cylindrical section with the opening/closing transmitting portion being inserted therein, and which is configured to guide the opening/closing transmitting portion; and
   an acting force transmitting portion that is fixed to the second sheath section, the probe fixed portion of the first sheath section being attached to the acting force transmitting portion from the distal direction side such that the probe fixed portion is rotatable with respect to the acting force transmitting portion in the periaxial directions of the longitudinal axis, the acting force transmitting portion being configured to transmit an acting force from the probe fixed portion to the bending cylindrical section toward the proximal direction, the acting force being configured to act on the probe fixed portion from the movable portion toward the proximal direction in a state that the movable portion moves toward the proximal direction and the jaw closes relative to the probe.

2. The grasping treatment device according to claim 1, further comprising a bending transmitting portion which is extended in the second sheath section along the longitudinal axis, and which is configured to move along the longitudinal axis to bend the bending cylindrical section,
   wherein the bending cylindrical section includes an active bending portion which has a higher rigidity than the guide member, and which is configured to actively bend in response to movement of the bending transmitting portion, the acting force toward the proximal direction being configured to be transmitted to the active bending portion from the acting force transmitting portion.

3. The grasping treatment device according to claim 2, wherein the acting force transmitting portion is coupled with the active bending portion in a state that the acting force transmitting portion abuts on the probe fixed portion irrespective of a rotating state of the grasping section and the first sheath section relative to the second sheath section.

4. The grasping treatment device according to claim 2, further comprising an operation unit which is provided to the proximal direction side of the second sheath section, the operation unit including a rotating operating section which is configured to perform a rotating operation of rotating the grasping section and the first sheath section, an opening/closing operating section which is configured to perform an opening/closing operation of opening or closing the jaw, and a bending operating section which is configured to perform a bending operation of bending the bending cylindrical section.

5. The grasping treatment device according to claim 4, wherein the rotating operating section is configured to rotate in one of the periaxial directions of the longitudinal axis to rotate the rotating transmitting portion, and
   the bending operating section is provided to the distal direction side of the rotating operating section, and is configured to rotate about a rotating axis perpendicular to the longitudinal axis to move the bending transmitting portion along the longitudinal axis.

6. The grasping treatment device according to claim 5, wherein the operation unit includes a cylindrical case which is extended along the longitudinal axis, and to which the rotating operating section and the bending operating section are attached, the opening/closing operating section includes a fixed handle which is extended from the cylindrical case to be away from the longitudinal axis, and a movable handle which is provided to the distal direction side of the fixed handle and which is openable/closeable relative to the fixed handle, the fixed handle includes a fixed side holding portion which is configured to be held in the opening/closing operation, and which has an absolute angle that is not smaller than 45° and not greater than 90° relative to the proximal direction on a reference plane, the reference plane being parallel to the longitudinal axis and also being parallel to the rotating axis, the movable handle includes a movable side holding portion which is configured to be held in the opening/closing operation, and which has a relative angle that is not smaller than 0° and not greater than 30° relative to the fixed side holding portion on the reference plane in a state that the movable handle is most-opened relative to the fixed handle, and the rotating operating section is placed in a range between a first extension line extending from the fixed side holding portion toward the cylindrical case and a second extension line extending from the movable side holding portion toward the cylindrical case on the reference plane.

7. The grasping treatment device according to claim 1, further comprising an ultrasonic generating section which is provided in the first sheath section being fixed to the probe, and which is configured to generate ultrasonic vibration, to be transmitted to the probe, when an electrical current is supplied thereto.

8. The grasping treatment device according to claim 1, wherein the acting force transmitting portion is located between the first sheath section and the bending cylindrical section in a direction along the longitudinal axis.

9. The grasping treatment device according to claim 1, wherein each of a proximal end of the opening/closing transmitting portion and a proximal end of the rotating transmitting portion is located on the proximal direction side with respect to the acting force transmitting portion.

10. The grasping treatment device according to claim 1, wherein the first sheath section is a separated body from the jaw.

11. The grasping treatment device according to claim 1, wherein the jaw is pivotally attached to the probe fixed portion.

* * * * *